(12) United States Patent
Chappa et al.

(10) Patent No.: US 9,827,401 B2
(45) Date of Patent: Nov. 28, 2017

(54) APPARATUS AND METHODS FOR COATING MEDICAL DEVICES

(71) Applicant: SurModics, Inc., Eden Prairie, MN (US)

(72) Inventors: Ralph A. Chappa, Ham Lake, MN (US); Andrew G. Bach, Edina, MN (US); Mark MacGregor, St. Paul, MN (US)

(73) Assignee: Surmodics, Inc., Eden Prairie, MN (US)

( * ) Notice: Subject to any disclaimer, the term of this patent is extended or adjusted under 35 U.S.C. 154(b) by 476 days.

(21) Appl. No.: 14/272,204

(22) Filed: May 7, 2014

(65) Prior Publication Data

US 2014/0328998 A1 Nov. 6, 2014

Related U.S. Application Data

(63) Continuation-in-part of application No. 13/906,599, filed on May 31, 2013.

(60) Provisional application No. 61/654,403, filed on Jun. 1, 2012, provisional application No. 61/661,684, filed on Jun. 19, 2012, provisional application No. 61/820,223, filed on May 7, 2013, provisional application No. 61/829,375, filed on May 31, 2013, (Continued)

(51) Int. Cl.
*A61M 25/10* (2013.01)
*B05B 13/04* (2006.01)

(52) U.S. Cl.
CPC ..... *A61M 25/1029* (2013.01); *B05B 13/0442* (2013.01); *A61M 2025/1031* (2013.01)

(58) Field of Classification Search
CPC .................................................. B05C 5/0241
See application file for complete search history.

(56) References Cited

U.S. PATENT DOCUMENTS

| 273,410 A | 3/1883 | Wadleigh et al. |
|---|---|---|
| 554,114 A | 2/1896 | Evertz |

(Continued)

FOREIGN PATENT DOCUMENTS

| CA | 2351016 | 12/2001 |
|---|---|---|
| DE | 3335502 | 3/1985 |

(Continued)

OTHER PUBLICATIONS

"Communication Pursuant to Rules 161 and 162 EPC," for European Patent Application No. 13729853.5, dated Feb. 13, 2015 (2 pages).

(Continued)

*Primary Examiner* — Cachet I Sellman
(74) *Attorney, Agent, or Firm* — Pauly, DeVries Smith & Deffner LLC

(57) ABSTRACT

Embodiments of the invention include apparatus and methods for coating drug eluting medical devices. In an embodiment, the invention includes a coating apparatus including a coating application unit comprising a movement restriction structure; a fluid applicator; and an air nozzle. The apparatus can further include a rotation mechanism and an axial motion mechanism, the axial motion mechanism configured to cause movement of at least one of the coating application unit and the rotation mechanism with respect to one another. Other embodiments are also included herein.

22 Claims, 19 Drawing Sheets

Related U.S. Application Data provisional application No. 61/875,524, filed on Sep. 9, 2013.

(56) References Cited

U.S. PATENT DOCUMENTS

| | | |
|---|---|---|
| 1,281,672 A | 10/1918 | Schorn |
| 1,866,100 A | 7/1932 | Hach |
| 2,253,019 A | 8/1941 | Crepeau |
| 2,330,880 A | 10/1943 | Gladfelter et al. |
| 2,335,116 A | 11/1943 | Hansen |
| 2,493,787 A | 1/1950 | Torretti |
| 2,781,280 A | 2/1957 | Miller |
| 2,821,158 A | 1/1958 | Brown |
| 3,198,170 A | 8/1965 | Toshio |
| 3,318,281 A | 5/1967 | Plegat |
| 3,416,530 A | 12/1968 | Ness |
| 3,625,214 A | 12/1971 | Higuchi |
| 3,669,917 A | 6/1972 | Ando et al. |
| 3,699,917 A | 10/1972 | Deverse et al. |
| 3,723,120 A | 3/1973 | Hummel et al. |
| 3,837,805 A | 9/1974 | Boucher |
| 3,935,896 A | 2/1976 | Tegtmeier et al. |
| 3,936,549 A | 2/1976 | Kohler et al. |
| 3,963,069 A | 6/1976 | Marti et al. |
| 3,966,120 A | 6/1976 | Furgalus et al. |
| 4,000,745 A | 1/1977 | Goldberg |
| 4,016,306 A | 4/1977 | Miyagawa et al. |
| 4,051,805 A | 10/1977 | Waldrum |
| 4,060,116 A | 11/1977 | Frailly |
| 4,069,307 A | 1/1978 | Higuchi et al. |
| 4,073,335 A | 2/1978 | Fort et al. |
| 4,075,975 A | 2/1978 | Oswald |
| 4,082,870 A | 4/1978 | Yenni |
| 4,144,317 A | 3/1979 | Higuchi et al. |
| 4,146,036 A | 3/1979 | Dutcher et al. |
| 4,148,934 A | 4/1979 | Baker |
| 4,153,201 A | 5/1979 | Berger et al. |
| 4,174,678 A | 11/1979 | Van Den Bergh |
| 4,195,637 A | 4/1980 | Gruntzig et al. |
| 4,196,231 A | 4/1980 | Hubers |
| 4,206,756 A | 6/1980 | Grossan |
| 4,209,019 A | 6/1980 | Dutcher et al. |
| 4,240,373 A | 12/1980 | Anger |
| 4,289,089 A | 9/1981 | Tacke et al. |
| 4,292,965 A | 10/1981 | Nash |
| 4,300,557 A | 11/1981 | Refojo et al. |
| 4,301,968 A | 11/1981 | Berger et al. |
| 4,304,765 A | 12/1981 | Shell et al. |
| 4,337,896 A | 7/1982 | Berger et al. |
| 4,352,459 A | 10/1982 | Berger et al. |
| 4,364,879 A | 12/1982 | Gut et al. |
| 4,375,820 A | 3/1983 | Vinarcsik et al. |
| 4,415,654 A | 11/1983 | Pohl |
| 4,475,972 A | 10/1984 | Wong |
| 4,503,802 A | 3/1985 | Keller et al. |
| 4,541,564 A | 9/1985 | Berger et al. |
| 4,544,626 A | 10/1985 | Sullivan |
| 4,567,934 A | 2/1986 | Nakao et al. |
| 4,572,451 A | 2/1986 | Ikeda et al. |
| 4,575,330 A | 3/1986 | Hull |
| 4,603,058 A | 7/1986 | Adams |
| 4,616,593 A | 10/1986 | Kawamura et al. |
| 4,622,917 A | 11/1986 | Schramm |
| 4,638,045 A | 1/1987 | Kohn et al. |
| 4,655,393 A | 4/1987 | Berger |
| 4,678,466 A | 7/1987 | Rosenwald |
| 4,723,708 A | 2/1988 | Berger et al. |
| 4,743,252 A | 5/1988 | Martin, Jr. et al. |
| 4,764,377 A | 8/1988 | Goodson |
| 4,819,661 A | 4/1989 | Heil et al. |
| 4,824,017 A | 4/1989 | Mansfield |
| 4,853,224 A | 8/1989 | Wong |
| 4,863,457 A | 9/1989 | Lee et al. |
| 4,892,736 A | 1/1990 | Goodson |
| 4,927,741 A | 5/1990 | Garth et al. |
| 4,953,564 A | 9/1990 | Berthelsen |
| 4,959,217 A | 9/1990 | Sanders et al. |
| 4,971,895 A | 11/1990 | Sullivan |
| 4,972,848 A | 11/1990 | Di Domenico et al. |
| 4,978,067 A | 12/1990 | Berger et al. |
| 4,988,883 A | 1/1991 | Oppawsky |
| 4,997,652 A | 3/1991 | Wong et al. |
| 5,002,067 A | 3/1991 | Berthelsen et al. |
| 5,002,582 A | 3/1991 | Guire et al. |
| 5,003,992 A | 4/1991 | Holleman et al. |
| 5,036,634 A | 8/1991 | Lessard et al. |
| 5,041,089 A | 8/1991 | Mueller et al. |
| 5,049,404 A | 9/1991 | Kisler et al. |
| 5,069,940 A | 12/1991 | Wenrick |
| 5,071,337 A | 12/1991 | Heller et al. |
| 5,076,285 A | 12/1991 | Hess et al. |
| 5,076,974 A | 12/1991 | Modrek et al. |
| 5,087,246 A | 2/1992 | Smith |
| 5,098,443 A | 3/1992 | Parel et al. |
| 5,102,402 A | 4/1992 | Dror et al. |
| 5,114,719 A | 5/1992 | Sabel et al. |
| 5,120,312 A | 6/1992 | Wigness et al. |
| 5,164,188 A | 11/1992 | Wong |
| 5,183,509 A | 2/1993 | Brown et al. |
| 5,207,343 A | 5/1993 | Bogadi |
| 5,219,120 A | 6/1993 | Ehrenberg et al. |
| 5,219,690 A | 6/1993 | Hammond |
| 5,221,698 A | 6/1993 | Amiden et al. |
| 5,229,128 A | 7/1993 | Haddad et al. |
| 5,246,867 A | 9/1993 | Maliwal et al. |
| 5,248,752 A | 9/1993 | Argyropoulos et al. |
| 5,254,164 A | 10/1993 | Masahumi |
| 5,255,693 A | 10/1993 | Dutcher et al. |
| 5,300,108 A | 4/1994 | Rebell et al. |
| 5,300,114 A | 4/1994 | Gwon |
| 5,304,121 A | 4/1994 | Sahatjian |
| 5,310,559 A | 5/1994 | Shah et al. |
| 5,314,419 A | 5/1994 | Pelling et al. |
| 5,318,587 A | 6/1994 | Davey |
| 5,324,325 A | 6/1994 | Moaddeb |
| 5,344,298 A | 9/1994 | Hull |
| 5,364,343 A | 11/1994 | Apolet et al. |
| 5,372,577 A | 12/1994 | Ungerleider |
| 5,378,475 A | 1/1995 | Smith et al. |
| 5,382,234 A | 1/1995 | Cornelius et al. |
| 5,385,148 A | 1/1995 | Lesh et al. |
| 5,387,247 A | 2/1995 | Vallana et al. |
| 5,395,618 A | 3/1995 | Darougar et al. |
| 5,405,376 A | 4/1995 | Mulier et al. |
| 5,405,631 A | 4/1995 | Rosenthal |
| 5,413,638 A | 5/1995 | Bernstein, Jr. et al. |
| 5,414,075 A | 5/1995 | Swan et al. |
| 5,421,979 A | 6/1995 | Stevenson |
| 5,423,777 A | 6/1995 | Tajiri et al. |
| 5,431,649 A | 7/1995 | Mulier et al. |
| 5,437,656 A | 8/1995 | Shikani et al. |
| 5,443,505 A | 8/1995 | Wong et al. |
| 5,447,724 A | 9/1995 | Helmus et al. |
| 5,449,382 A | 9/1995 | Dayton |
| 5,464,650 A | 11/1995 | Berg et al. |
| 5,466,233 A | 11/1995 | Weiner et al. |
| 5,472,436 A | 12/1995 | Fremstad |
| 5,476,511 A | 12/1995 | Gwon et al. |
| 5,501,735 A | 3/1996 | Pender |
| 5,501,856 A | 3/1996 | Ohtori et al. |
| 5,512,055 A | 4/1996 | Domb et al. |
| 5,525,348 A | 6/1996 | Whitbourne et al. |
| 5,527,389 A | 6/1996 | Rosenblum et al. |
| 5,545,208 A | 8/1996 | Wolff et al. |
| 5,556,633 A | 9/1996 | Haddad et al. |
| 5,571,089 A | 11/1996 | Crocker |
| 5,578,075 A | 11/1996 | Dayton |
| 5,582,616 A | 12/1996 | Bolduc et al. |
| 5,591,227 A | 1/1997 | Dinh et al. |
| 5,605,696 A | 2/1997 | Eury et al. |
| 5,609,629 A | 3/1997 | Fearnot et al. |
| 5,624,411 A | 4/1997 | Tuch |
| 5,624,975 A | 4/1997 | Valencia |
| 5,626,919 A | 5/1997 | Chapman et al. |

(56) References Cited

U.S. PATENT DOCUMENTS

| | | |
|---|---|---|
| 5,630,879 A | 5/1997 | Eichmann et al. |
| 5,637,113 A | 6/1997 | Tartaglia et al. |
| 5,637,460 A | 6/1997 | Swan et al. |
| 5,643,362 A | 7/1997 | Garves |
| 5,645,592 A | 7/1997 | Nicolais et al. |
| 5,651,986 A | 7/1997 | Brem |
| 5,656,332 A | 8/1997 | Saito et al. |
| 5,658,387 A | 8/1997 | Reardon et al. |
| 5,673,473 A | 10/1997 | Johnson et al. |
| 5,679,400 A | 10/1997 | Tuch |
| 5,714,360 A | 2/1998 | Swan et al. |
| 5,725,493 A | 3/1998 | Avery et al. |
| 5,743,964 A | 4/1998 | Pankake |
| 5,766,242 A | 6/1998 | Wong et al. |
| 5,773,019 A | 6/1998 | Ashton et al. |
| 5,776,101 A | 7/1998 | Goy |
| 5,807,331 A | 9/1998 | Den Heijer et al. |
| 5,807,395 A | 9/1998 | Mulier et al. |
| 5,810,836 A | 9/1998 | Hussein et al. |
| 5,824,072 A | 10/1998 | Wong |
| 5,830,173 A | 11/1998 | Avery et al. |
| 5,833,715 A | 11/1998 | Vachon et al. |
| 5,833,891 A | 11/1998 | Subramaniam et al. |
| 5,837,008 A | 11/1998 | Berg et al. |
| 5,837,088 A | 11/1998 | Palmgren et al. |
| 5,837,313 A | 11/1998 | Ding et al. |
| 5,849,359 A | 12/1998 | Burns et al. |
| 5,858,435 A | 1/1999 | Gallo |
| 5,868,697 A | 2/1999 | Richter et al. |
| 5,877,224 A | 3/1999 | Brocchini et al. |
| 5,882,336 A | 3/1999 | Janacek |
| 5,882,405 A | 3/1999 | Kish et al. |
| 5,886,026 A | 3/1999 | Hunter et al. |
| 5,897,911 A | 4/1999 | Loeffler |
| 5,904,144 A | 5/1999 | Hammang et al. |
| 5,913,653 A | 6/1999 | Kempf |
| 5,921,982 A | 7/1999 | Lesh et al. |
| 5,925,885 A | 7/1999 | Clark et al. |
| 5,928,662 A | 7/1999 | Phillips |
| 5,972,027 A | 10/1999 | Johnson |
| 5,972,369 A | 10/1999 | Roorda et al. |
| 5,976,256 A | 11/1999 | Kawano |
| 5,980,972 A | 11/1999 | Ding |
| 5,989,579 A | 11/1999 | Darougar et al. |
| 5,997,517 A | 12/1999 | Whitbourne |
| 6,001,386 A | 12/1999 | Ashton et al. |
| 6,001,425 A | 12/1999 | Stash et al. |
| 6,019,784 A | 2/2000 | Hines |
| 6,033,582 A | 3/2000 | Lee et al. |
| 6,053,924 A | 4/2000 | Hussein |
| 6,056,998 A | 5/2000 | Fujimoto |
| 6,074,661 A | 6/2000 | Olejnik et al. |
| 6,091,978 A | 7/2000 | Johnson et al. |
| 6,094,887 A | 8/2000 | Swank et al. |
| 6,096,070 A | 8/2000 | Ragheb et al. |
| 6,099,562 A | 8/2000 | Ding et al. |
| 6,102,887 A | 8/2000 | Altman |
| 6,110,483 A | 8/2000 | Whitbourne et al. |
| 6,117,456 A | 9/2000 | Lee et al. |
| 6,120,536 A | 9/2000 | Ding et al. |
| 6,129,933 A | 10/2000 | Oshlack et al. |
| 6,143,037 A | 11/2000 | Goldstein et al. |
| 6,153,252 A | 11/2000 | Hossainy et al. |
| 6,156,373 A | 12/2000 | Zhong et al. |
| 6,165,526 A | 12/2000 | Newman et al. |
| 6,177,095 B1 | 1/2001 | Sawhney et al. |
| 6,187,370 B1 | 2/2001 | Dinh et al. |
| 6,197,324 B1 | 3/2001 | Crittenden |
| 6,203,551 B1 | 3/2001 | Wu |
| 6,203,556 B1 | 3/2001 | Evans et al. |
| 6,203,732 B1 | 3/2001 | Clubb et al. |
| 6,207,337 B1 | 3/2001 | Swain |
| 6,212,434 B1 | 4/2001 | Scheiner et al. |
| 6,214,008 B1 | 4/2001 | Illi |
| 6,214,115 B1 | 4/2001 | Taylor et al. |
| 6,214,901 B1 | 4/2001 | Chudzik et al. |
| 6,217,895 B1 | 4/2001 | Guo et al. |
| 6,218,016 B1 | 4/2001 | Tedeschi |
| 6,245,089 B1 | 6/2001 | Daniel et al. |
| 6,245,099 B1 | 6/2001 | Edwin et al. |
| 6,248,112 B1 | 6/2001 | Gambale et al. |
| 6,251,090 B1 | 6/2001 | Avery et al. |
| 6,251,136 B1 | 6/2001 | Guruwaiya et al. |
| 6,251,418 B1 | 6/2001 | Ahern et al. |
| 6,254,921 B1 | 7/2001 | Chappa et al. |
| 6,278,018 B1 | 8/2001 | Swan |
| 6,279,505 B1 | 8/2001 | Plester et al. |
| 6,287,285 B1 | 9/2001 | Michal et al. |
| 6,290,728 B1 | 9/2001 | Phelps et al. |
| 6,298,272 B1 | 10/2001 | Peterfeso et al. |
| 6,303,148 B1 | 10/2001 | Hennink et al. |
| 6,306,125 B1 | 10/2001 | Parker et al. |
| 6,306,426 B1 | 10/2001 | Olejnik et al. |
| 6,309,370 B1 | 10/2001 | Haim et al. |
| 6,322,847 B1 | 11/2001 | Zhong et al. |
| RE37,463 E | 12/2001 | Altman |
| 6,331,313 B1 | 12/2001 | Wong et al. |
| 6,333,595 B1 | 12/2001 | Horikawa et al. |
| 6,344,035 B1 | 2/2002 | Chudzik et al. |
| 6,345,630 B2 | 2/2002 | Fishkin et al. |
| 6,358,247 B1 | 3/2002 | Altman et al. |
| 6,358,556 B1 | 3/2002 | Ding et al. |
| 6,360,129 B1 | 3/2002 | Ley et al. |
| 6,368,658 B1 | 4/2002 | Schwarz et al. |
| 6,375,972 B1 | 4/2002 | Guo et al. |
| 6,394,995 B1 | 5/2002 | Solar et al. |
| 6,395,326 B1 | 5/2002 | Castro et al. |
| 6,399,144 B2 | 6/2002 | Dinh et al. |
| 6,399,655 B1 | 6/2002 | De et al. |
| 6,399,704 B1 | 6/2002 | Laurin et al. |
| 6,406,754 B2 | 6/2002 | Chappa et al. |
| 6,431,770 B1 | 8/2002 | Kurematsu et al. |
| 6,435,959 B1 | 8/2002 | Skrmetta |
| 6,451,373 B1 | 9/2002 | Hossainy et al. |
| 6,478,776 B1 | 11/2002 | Rosenman et al. |
| 6,497,691 B1 | 12/2002 | Bevins et al. |
| 6,501,994 B1 | 12/2002 | Janke et al. |
| 6,505,082 B1 | 1/2003 | Scheiner et al. |
| 6,506,411 B2 | 1/2003 | Hunter et al. |
| 6,506,437 B1 | 1/2003 | Harish et al. |
| 6,517,515 B1 | 2/2003 | Eidenschink |
| 6,517,889 B1 | 2/2003 | Jayaraman |
| 6,521,299 B1 | 2/2003 | Dessauer |
| 6,527,863 B1 | 3/2003 | Pacetti et al. |
| 6,544,544 B2 | 4/2003 | Hunter et al. |
| 6,544,582 B1 | 4/2003 | Yoe |
| 6,547,787 B1 | 4/2003 | Altman et al. |
| 6,548,078 B2 | 4/2003 | Guo et al. |
| 6,555,157 B1 | 4/2003 | Hossainy |
| 6,559,560 B1 | 5/2003 | Jin et al. |
| 6,562,051 B1 | 5/2003 | Bolduc et al. |
| 6,562,136 B1 | 5/2003 | Chappa et al. |
| 6,565,659 B1 | 5/2003 | Pacetti et al. |
| 6,572,644 B1 | 6/2003 | Moein |
| 6,585,764 B2 | 7/2003 | Wright et al. |
| 6,595,958 B1 | 7/2003 | Mickley |
| 6,599,560 B1 | 7/2003 | Daggett et al. |
| 6,605,154 B1 | 8/2003 | Villareal |
| 6,607,598 B2 | 8/2003 | Schwarz et al. |
| 6,613,017 B1 | 9/2003 | Mickley |
| 6,616,765 B1 | 9/2003 | Castro et al. |
| 6,623,504 B2 | 9/2003 | Vrba et al. |
| 6,653,426 B2 | 11/2003 | Alvarado et al. |
| 6,656,529 B1 | 12/2003 | Pankake |
| 6,669,980 B2 | 12/2003 | Hansen |
| 6,669,994 B2 | 12/2003 | Swan et al. |
| 6,673,154 B1 | 1/2004 | Pacetti et al. |
| 6,676,987 B2 | 1/2004 | Zhong et al. |
| 6,695,920 B1 | 2/2004 | Pacetti et al. |
| 6,706,023 B1 | 3/2004 | Huttner et al. |
| 6,709,514 B1 | 3/2004 | Hossainy |
| 6,709,712 B2 | 3/2004 | Chappa et al. |
| 6,713,081 B2 | 3/2004 | Robinson et al. |
| 6,716,081 B2 | 4/2004 | Kim et al. |

(56) References Cited

U.S. PATENT DOCUMENTS

| | | |
|---|---|---|
| 6,716,196 B2 | 4/2004 | Lesh et al. |
| 6,719,750 B2 | 4/2004 | Varner et al. |
| 6,719,805 B1 | 4/2004 | Ahern |
| 6,723,373 B1 | 4/2004 | Narayanan et al. |
| 6,725,901 B1 | 4/2004 | Kramer et al. |
| 6,726,918 B1 | 4/2004 | Wong et al. |
| 6,743,233 B1 | 6/2004 | Baldwin et al. |
| 6,743,462 B1 | 6/2004 | Pacetti |
| 6,743,463 B2 | 6/2004 | Weber et al. |
| 6,752,959 B2 | 6/2004 | Smith et al. |
| 6,764,470 B2 | 7/2004 | Dimick |
| 6,783,793 B1 | 8/2004 | Hossainy et al. |
| 6,803,070 B2 | 10/2004 | Weber |
| 6,818,063 B1 | 11/2004 | Kerrigan |
| 6,896,842 B1 | 5/2005 | Hamilton et al. |
| 6,981,982 B2 | 1/2006 | Armstrong et al. |
| 7,010,933 B2 | 3/2006 | Ishitomi et al. |
| 7,041,174 B2 | 5/2006 | Carlson et al. |
| 7,045,015 B2 | 5/2006 | Renn et al. |
| 7,077,848 B1 | 7/2006 | De Juan, Jr. et al. |
| 7,077,910 B2 | 7/2006 | Chappa et al. |
| 7,087,658 B2 | 8/2006 | Swan et al. |
| 7,105,350 B2 | 9/2006 | Foster et al. |
| 7,125,577 B2 | 10/2006 | Chappa |
| 7,163,523 B2 | 1/2007 | Devens, Jr. et al. |
| 7,186,374 B2 | 3/2007 | Zelina et al. |
| 7,192,484 B2 | 3/2007 | Chappa et al. |
| 7,198,675 B2 | 4/2007 | Fox et al. |
| 7,335,314 B2 | 2/2008 | Wu |
| 7,563,324 B1 | 7/2009 | Chen et al. |
| 7,611,532 B2 | 11/2009 | Bates et al. |
| 7,638,156 B1 | 12/2009 | Kokish et al. |
| 7,669,548 B2 | 3/2010 | Chappa |
| 7,883,749 B2 | 2/2011 | Carlson |
| 7,958,840 B2 | 6/2011 | Chappa |
| 8,003,156 B2 | 8/2011 | Van Sciver |
| 8,166,909 B2 | 5/2012 | Chappa |
| 8,246,974 B2 | 8/2012 | Chappa |
| 8,318,263 B2 | 11/2012 | Carlson et al. |
| 8,632,837 B2 | 1/2014 | Gong et al. |
| 9,283,350 B2 | 3/2016 | Chappa et al. |
| 9,308,355 B2 | 4/2016 | Chappa et al. |
| 9,364,349 B2 | 6/2016 | Chappa et al. |
| 2001/0001824 A1 | 5/2001 | Wu |
| 2001/0014717 A1 | 8/2001 | Hossainy et al. |
| 2001/0022988 A1 | 9/2001 | Schwarz et al. |
| 2001/0026834 A1 | 10/2001 | Chappa et al. |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0013298 A1 | 1/2002 | Hunter |
| 2002/0018795 A1 | 2/2002 | Whitbourne et al. |
| 2002/0026176 A1 | 2/2002 | Varner et al. |
| 2002/0026236 A1 | 2/2002 | Helmus et al. |
| 2002/0032434 A1 | 3/2002 | Chudzik et al. |
| 2002/0032477 A1 | 3/2002 | Helmus et al. |
| 2002/0046521 A1 | 4/2002 | Steinacker, Sr. et al. |
| 2002/0051730 A1 | 5/2002 | Bodnar et al. |
| 2002/0054900 A1 | 5/2002 | Kamath et al. |
| 2002/0062730 A1 | 5/2002 | Thornton |
| 2002/0082679 A1 | 6/2002 | Sirhan et al. |
| 2002/0091433 A1 | 7/2002 | Ding et al. |
| 2002/0094440 A1 | 7/2002 | Llanos et al. |
| 2002/0103526 A1 | 8/2002 | Steinke |
| 2002/0107330 A1 | 8/2002 | Pinchuk et al. |
| 2002/0111590 A1 | 8/2002 | Davila et al. |
| 2002/0114823 A1 | 8/2002 | Sirhan et al. |
| 2002/0115400 A1 | 8/2002 | Skrmetta |
| 2002/0120326 A1 | 8/2002 | Michal |
| 2002/0133183 A1 | 9/2002 | Lentz et al. |
| 2002/0138048 A1 | 9/2002 | Tuch |
| 2002/0155212 A1 | 10/2002 | Hossainy |
| 2002/0159915 A1 | 10/2002 | Zelina et al. |
| 2002/0165265 A1 | 11/2002 | Hunter et al. |
| 2002/0168394 A1 | 11/2002 | Hossainy et al. |
| 2002/0188037 A1 | 12/2002 | Chudzik et al. |
| 2002/0188170 A1 | 12/2002 | Santamore et al. |
| 2002/0198511 A1 | 12/2002 | Varner et al. |
| 2003/0003221 A1 | 1/2003 | Zhong et al. |
| 2003/0004209 A1 | 1/2003 | Hunter et al. |
| 2003/0014036 A1 | 1/2003 | Varner et al. |
| 2003/0021828 A1 | 1/2003 | Guo et al. |
| 2003/0031780 A1 | 2/2003 | Chudzik et al. |
| 2003/0039689 A1 | 2/2003 | Chen et al. |
| 2003/0044514 A1 | 3/2003 | Richard |
| 2003/0054023 A1 | 3/2003 | Hughes et al. |
| 2003/0054090 A1 | 3/2003 | Hansen |
| 2003/0059520 A1 | 3/2003 | Chen et al. |
| 2003/0059920 A1 | 3/2003 | Drohan et al. |
| 2003/0060783 A1 | 3/2003 | Koole et al. |
| 2003/0065332 A1 | 4/2003 | Tenhuisen et al. |
| 2003/0083646 A1 | 5/2003 | Sirhan et al. |
| 2003/0088307 A1 | 5/2003 | Shulze et al. |
| 2003/0094736 A1 | 5/2003 | Qin et al. |
| 2003/0096131 A1 | 5/2003 | Beavers |
| 2003/0113439 A1 | 6/2003 | Pacetti et al. |
| 2003/0120200 A1 | 6/2003 | Bergheim et al. |
| 2003/0143315 A1 | 7/2003 | Pui et al. |
| 2003/0150380 A1 | 8/2003 | Yoe |
| 2003/0157187 A1 | 8/2003 | Hunter |
| 2003/0157241 A1 | 8/2003 | Hossainy et al. |
| 2003/0158598 A1 | 8/2003 | Ashton et al. |
| 2003/0161937 A1 | 8/2003 | Leiby et al. |
| 2003/0165613 A1 | 9/2003 | Chappa et al. |
| 2003/0175324 A1 | 9/2003 | Robinson et al. |
| 2003/0181848 A1 | 9/2003 | Bergheim et al. |
| 2003/0190420 A1 | 10/2003 | Chappa et al. |
| 2003/0207856 A1 | 11/2003 | Tremble et al. |
| 2003/0215564 A1 | 11/2003 | Heller et al. |
| 2003/0229333 A1 | 12/2003 | Ashton et al. |
| 2003/0232087 A1 | 12/2003 | Lawin et al. |
| 2003/0232122 A1 | 12/2003 | Chappa et al. |
| 2003/0236513 A1 | 12/2003 | Schwarz et al. |
| 2003/0236514 A1 | 12/2003 | Schwarz |
| 2004/0006146 A1 | 1/2004 | Evans et al. |
| 2004/0022853 A1 | 2/2004 | Ashton et al. |
| 2004/0034357 A1 | 2/2004 | Beane et al. |
| 2004/0037886 A1 | 2/2004 | Hsu |
| 2004/0044404 A1 | 3/2004 | Stucke et al. |
| 2004/0047911 A1 | 3/2004 | Lyu et al. |
| 2004/0062592 A1 | 4/2004 | Shekalim et al. |
| 2004/0062875 A1 | 4/2004 | Chappa et al. |
| 2004/0073298 A1 | 4/2004 | Hossainy |
| 2004/0081745 A1 | 4/2004 | Hansen |
| 2004/0121014 A1 | 6/2004 | Guo et al. |
| 2004/0133155 A1 | 7/2004 | Varner et al. |
| 2004/0137059 A1 | 7/2004 | Nivaggioli et al. |
| 2004/0142013 A1 | 7/2004 | Rubsamen |
| 2004/0143314 A1 | 7/2004 | Sommer et al. |
| 2004/0161547 A1 | 8/2004 | Carlson et al. |
| 2004/0185168 A1 | 9/2004 | Weber et al. |
| 2004/0194704 A1 | 10/2004 | Chappa et al. |
| 2004/0211362 A1 | 10/2004 | Castro et al. |
| 2004/0213893 A1 | 10/2004 | Boulais |
| 2005/0019371 A1 | 1/2005 | Anderson et al. |
| 2005/0059956 A1 | 3/2005 | Varner et al. |
| 2005/0098097 A1 | 5/2005 | Chen et al. |
| 2005/0129732 A1 | 6/2005 | Rubsamen |
| 2005/0142070 A1 | 6/2005 | Hartley |
| 2005/0143363 A1 | 6/2005 | De Juan et al. |
| 2005/0147690 A1 | 7/2005 | Masters et al. |
| 2005/0158449 A1 | 7/2005 | Chappa |
| 2005/0196518 A1 | 9/2005 | Stenzel et al. |
| 2005/0233061 A1 | 10/2005 | Schwarz et al. |
| 2005/0233062 A1 | 10/2005 | Hossainy et al. |
| 2005/0240147 A1 | 10/2005 | Makower et al. |
| 2005/0255142 A1 | 11/2005 | Chudzik et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0281863 A1 | 12/2005 | Anderson et al. |
| 2005/0287188 A1 | 12/2005 | Anderson et al. |

(56) References Cited

U.S. PATENT DOCUMENTS

| | | |
|---|---|---|
| 2006/0020295 A1 | 1/2006 | Brockway et al. |
| 2006/0029720 A1 | 2/2006 | Panos et al. |
| 2006/0045981 A1 | 3/2006 | Tsushi et al. |
| 2006/0059520 A1 | 3/2006 | Miyazawa et al. |
| 2006/0064134 A1 | 3/2006 | Mazar et al. |
| 2006/0064142 A1 | 3/2006 | Chavan et al. |
| 2006/0074404 A1 | 4/2006 | Struble |
| 2006/0088653 A1 | 4/2006 | Chappa |
| 2006/0096535 A1 | 5/2006 | Haller et al. |
| 2006/0110428 A1 | 5/2006 | De Juan et al. |
| 2006/0111754 A1 | 5/2006 | Rezai et al. |
| 2006/0116590 A1 | 6/2006 | Fayram et al. |
| 2006/0165872 A1 | 7/2006 | Chappa et al. |
| 2006/0191476 A1 | 8/2006 | Nagase et al. |
| 2006/0269663 A1 | 11/2006 | Mori et al. |
| 2007/0065481 A1 | 3/2007 | Chudzik et al. |
| 2007/0101933 A1 | 5/2007 | Chappa |
| 2007/0116855 A1 | 5/2007 | Fox et al. |
| 2007/0131165 A1 | 6/2007 | Fox et al. |
| 2007/0141232 A1 | 6/2007 | Tochterman et al. |
| 2007/0259100 A1 | 11/2007 | Guerriero et al. |
| 2007/0259102 A1 | 11/2007 | Mcniven et al. |
| 2007/0259125 A1 | 11/2007 | O'brien et al. |
| 2007/0275175 A1 | 11/2007 | Hossainy |
| 2008/0149025 A1 | 6/2008 | Swenson |
| 2008/0179781 A1 | 7/2008 | Iwata |
| 2008/0274266 A1 | 11/2008 | Davis et al. |
| 2009/0018643 A1 | 1/2009 | Hashi et al. |
| 2009/0054837 A1 | 2/2009 | Von Holst et al. |
| 2009/0090299 A1 | 4/2009 | Menendez et al. |
| 2009/0176030 A1 | 7/2009 | Carlson et al. |
| 2009/0269481 A1 | 10/2009 | Chappa et al. |
| 2010/0040766 A1 | 2/2010 | Chappa et al. |
| 2010/0055294 A1* | 3/2010 | Wang ............... B05D 1/002 427/2.25 |
| 2010/0070020 A1 | 3/2010 | Hashi et al. |
| 2010/0179475 A1 | 7/2010 | Hoffmann et al. |
| 2010/0227044 A1 | 9/2010 | Scheer |
| 2010/0272774 A1 | 10/2010 | Chappa et al. |
| 2010/0319183 A1 | 12/2010 | Hulseman et al. |
| 2011/0046724 A1 | 2/2011 | Heilmann et al. |
| 2011/0104392 A1 | 5/2011 | Carlson et al. |
| 2011/0238011 A1 | 9/2011 | Scheller et al. |
| 2011/0281019 A1 | 11/2011 | Gong et al. |
| 2011/0281020 A1* | 11/2011 | Gong ............... A61M 25/1029 427/2.1 |
| 2011/0311713 A1 | 12/2011 | O'neill et al. |
| 2011/0311764 A1 | 12/2011 | Hulseman et al. |
| 2012/0043693 A1 | 2/2012 | King et al. |
| 2012/0059317 A1 | 3/2012 | Michiyo et al. |
| 2012/0100279 A1 | 4/2012 | Neumann et al. |
| 2012/0315376 A1* | 12/2012 | Nguyen ............... B05C 5/02 427/2.28 |
| 2013/0337147 A1 | 12/2013 | Chappa et al. |
| 2014/0121597 A1 | 5/2014 | Chappa et al. |
| 2014/0161964 A1 | 6/2014 | Chappa et al. |
| 2016/0256668 A1 | 9/2016 | Chappa et al. |

FOREIGN PATENT DOCUMENTS

| | | |
|---|---|---|
| DE | 20200223 | 4/2002 |
| DE | 10053826 | 5/2002 |
| EP | 0096433 | 12/1983 |
| EP | 144873 | 6/1985 |
| EP | 414233 | 2/1991 |
| EP | 0604022 | 6/1994 |
| EP | 0623354 | 11/1994 |
| EP | 0716836 | 6/1996 |
| EP | 0734721 | 10/1996 |
| EP | 0747069 | 12/1996 |
| EP | 0857516 A2 | 2/1998 |
| EP | 0832655 | 4/1998 |
| EP | 0834282 | 4/1998 |
| EP | 0879595 | 11/1998 |
| EP | 0923953 | 6/1999 |
| EP | 0945148 | 9/1999 |
| EP | 1374924 | 1/2004 |
| EP | 1382302 | 1/2004 |
| EP | 1594623 | 4/2007 |
| EP | 1610836 | 8/2008 |
| EP | 2994241 | 3/2016 |
| FR | 1304457 | 8/1962 |
| FR | 2733163 | 10/1996 |
| GB | 525373 | 8/1940 |
| GB | 2301296 | 12/1996 |
| GB | 104464 | 4/2001 |
| JP | 57048354 | 3/1982 |
| JP | 63-011547 | 1/1988 |
| JP | 02-036882 | 2/1990 |
| JP | 06-246207 | 9/1994 |
| JP | 08-086466 | 4/1996 |
| JP | 09-038546 | 2/1997 |
| JP | 09-194347 | 7/1997 |
| JP | 2005059225 | 3/2005 |
| JP | 2015527092 | 9/2015 |
| JP | 2016504058 | 2/2016 |
| WO | 8905664 | 6/1989 |
| WO | 9112779 | 9/1991 |
| WO | 9211895 | 7/1992 |
| WO | 9215286 | 9/1992 |
| WO | 9300174 | 1/1993 |
| WO | 9315682 | 8/1993 |
| WO | 9421308 | 9/1994 |
| WO | 9421309 | 9/1994 |
| WO | 9503036 | 2/1995 |
| WO | 9710011 | 3/1997 |
| WO | 9737640 | 11/1997 |
| WO | 9817331 | 4/1998 |
| WO | 9832474 | 7/1998 |
| WO | 9901114 | 1/1999 |
| WO | 9858690 | 3/1999 |
| WO | 9936071 | 7/1999 |
| WO | 9938546 | 8/1999 |
| WO | 9955396 | 11/1999 |
| WO | 0001322 | 1/2000 |
| WO | 0002564 | 1/2000 |
| WO | 0012163 | 3/2000 |
| WO | 0021584 | 4/2000 |
| WO | 0121326 | 3/2001 |
| WO | 0132382 | 5/2001 |
| WO | 0178626 | 10/2001 |
| WO | 0194103 | 12/2001 |
| WO | 0209786 | 2/2002 |
| WO | 0220174 | 3/2002 |
| WO | 03004072 | 1/2003 |
| WO | 03024615 | 3/2003 |
| WO | 2004/028579 | 4/2004 |
| WO | 2004028579 | 4/2004 |
| WO | 2004028699 | 4/2004 |
| WO | 2004037126 | 5/2004 |
| WO | 2004037443 | 5/2004 |
| WO | 2004073885 | 9/2004 |
| WO | 2004091682 | 10/2004 |
| WO | 2004098565 | 11/2004 |
| WO | 2005009297 | 2/2005 |
| WO | 2006110366 | 10/2006 |
| WO | 2007059144 | 5/2007 |
| WO | 2007100801 | 9/2007 |
| WO | 2008002357 | 1/2008 |
| WO | 2009132214 | 10/2009 |
| WO | 2010024898 | 3/2010 |
| WO | 2010146096 | 12/2010 |
| WO | 2013181498 | 12/2013 |
| WO | 2014066760 | 5/2014 |
| WO | 2014182833 | 11/2014 |

OTHER PUBLICATIONS

"Final Office Action," for U.S. Appl. No. 13/906,599 dated Sep. 18, 2015 (35 pages).

"International Preliminary Report on Patentability," for PCT/US2014/037179 dated Nov. 19, 2015 (9 pages).

(56) References Cited

OTHER PUBLICATIONS

"Response Final Office Action," for U.S. Appl. No. 13/906,599, mailed Sep. 18, 2015 and filed with the USPTO Nov. 3, 2015 (6 pages).
"Response to Communication Pursuant to Rules 161 and 162 EPC," for European Patent Application No. 13729853.5, filed with the EPO Aug. 13, 2015 (21 pages).
"Response to Non-Final Office Action," for U.S. Appl. No. 13/906,599, mailed Apr. 9, 2015 and filed with the USPTO Aug. 10, 2015 (9 pages).
"Response to Non-Final Office Action," for U.S. Appl. No. 14/063,124, mailed Apr. 15, 2015 and filed with the USPTO Jul. 15, 2015 (14 pages).
"Communication Pursuant to Rules 161(1) and 162 EPC," for European Patent Application No. 14730319.2, dated Dec. 22, 2015 (2 pages).
"Non-Final Office Action," for U.S. Appl. No. 14/063,113, dated Mar. 28, 2016 (43 pages).
"Response to Communication Pursuant to Rules 161(1) and 162 EPC," for European Patent Application No. 13792526.9, mailed Jul. 7, 2015 and filed with the EPO Jan. 7, 2016 (18 pages).
File History for Related U.S. Appl. No. 10/371,043 downloaded Jul. 8, 2015, 222 pages.
Braun, Dietrich "Plastics," Concise Encyclopedia of Polymer Science and Engineering, 1990 (4 pages), 462-464.
"Cross-Link," http://en.wikipedia.org/wiki/Cross-link; retrieved Nov. 6, 2009 (4 pages) Nov. 6, 2009.
Di Mario, et al., "Radioactive Stents—A Dead End?," Current Interventional Cardiology Reports, 2000 (2 pages), 87-88.
"European Examination Report," for European Application No. 04 711 809.6 dated Jan. 23, 2006 (4 pages).
"European Examination Report," for Eurpoean Application No. 06740366.7, dated May 5, 2009 (4 pages).
"Eurpoean Examination Report," for European Application No. 04 759 211.8 dated Aug. 7, 2006 (5 pages).
File History for Related U.S. Appl. No. 10/409,434 downloaded Jul. 8, 2015, 199 pages.
File History for Related U.S. Appl. No. 10/976,193 downloaded Jul. 8, 2015, 446 pages.
File History for Related U.S. Appl. No. 10/976,348 downloaded Jul. 8, 2015, 219 pages.
File History for Related U.S. Appl. No. 11/102,465 downloaded Jul. 8, 2015, 500 pages.
File History for Related U.S. Appl. No. 11/375,487 downloaded Jul. 8, 2015, 301 pages.
File History for Related U.S. Appl. No. 11/421,637 downloaded Jul. 8, 2015, 193 pages.
File History for Related U.S. Appl. No. 11/539,443 downloaded Jul. 8, 2015, 269 pages.
File History for Related U.S. Appl. No. 11/559,817 downloaded Jul. 8, 2015, 302 pages.
File History for Related U.S. Appl. No. 11/823,055 downloaded Jul. 8, 2015, 156 pages.
File History for Related U.S. Appl. No. 12/109,139 downloaded Jul. 8, 2015, 213 pages.
File History for Related U.S. Appl. No. 12/980,920 downloaded Jul. 8, 2015, 141 pages.
File History for Related U.S. Appl. No. 13/906,599 downloaded Jul. 8, 2015, 117 pages.
File History for Related U.S. Appl. No. 14/063,113 downloaded Jul. 8, 2015, 92 pages.
File History for Related U.S. Appl. No. 14/063,124 downloaded Jul. 8, 2015, 125 pages.
"Final Office Action," for Japanese Application No. 2006-509776, dated Jul. 5, 2011, (7 pages).

"First Office Action," for CA Application No. 2604832, dated Mar. 16, 2012 (4 pages).
"First Office Action," for Japanese patent Application No. 2006-503609, dated Apr. 4, 2010 (7 pages) with English translation.
Hiemenz, Paul "Polymer Chemistry: The Basic Concepts," CRC Press, 1984 (2 pages), 9 & 12.
"International Preliminary Report on Patentability," for International Application No. PCT/US2005/038628 dated May 10, 2007 (10 pages).
"International Preliminary Report on Patentability," for PCT Application No. PCT/US2013/043547, dated Dec. 11, 2014 (7 pages).
"International Preliminary Report on Patentability," for PCT/US2013/066810, dated May 7, 2015 (12 pages).
"International Search Report & Written Opinion," for PCT/US2004/004486, dated Jul. 19, 2004 (8 pages).
"International Search Report & Written Opinion," for PCT/US2004/010692, dated Jul. 23, 2004 (9 pages).
"International Search Report and Written Opinion," for International Application No. PCT/US2005/038628 dated Mar. 22, 2006 (16 pages).
"International Search Report and Written Opinion," for PCT Application No. PCT/US2014/037179 dated Feb. 19, 2015 (15 pages).
"International Search Report and Written Opinion," for PCT/US2006/044218, dated Mar. 22, 2007 (12 pages).
"International Search Report and Written Opinion," for PCT/US2009/041575, dated Jul. 22, 2009 (15 pages).
"International Search Report and Written Opinion," for PCT/US2013/043547, dated Oct. 1, 2013 (10 pages).
"International Search Report and Written Opinion," for PCT/US2013/066810, dated Apr. 17, 2014 (18 pages).
"Invitation to Pay Additional Fees and, Where Applicable, Protest Fee," for PCT/US2013/066810, mailed Feb. 7, 2014 (6 pages).
"Invitation to Pay Additional Fees," for PCT Application No. PCT/US2014/037179, mailed Oct. 24, 2014 (5 pages).
"Notice of Allowance Received," for Japanese Application No. 2006-509776, dated Dec 1, 2011, (4 pages) including English translation.
"Response to European Examination Report," for European Application No. 06740366.7, filed Feb. 22, 2011 (8 pages).
"Ultrasonic Spray Nozzle Systems," SONO-TEK Corporation Brochure, 2005 (16 pages).
Yeo, Yoon "A New Microencapsulation Method Using an Ultrasonic Atomizer Based on Interfacial Solvent Exchange," Journal of Controlled Release 100 (2004) 379-388 (10 pages) 2004, 379-388.
"Response to Communication Pursuant to Rules 161(1) and 162 EPC," for European Patent Application No. 14730319.2, filed with the EPO Jun. 24, 2016 (11 pages).
"Response to Non-Final Office Action," for U.S. Appl. No. 14/063,113, mailed Mar. 28, 2016 and filed with the USPTO Jun. 24, 2016 (11 pages).
"Notice of Allowance," for U.S. Appl. No. 15/061,234, dated Dec. 16, 2016 (11 pages).
"Response to Final Office Action," for U.S. Appl. No. 14/063,113, mailed Oct. 17, 2016 and filed with the USPTO Dec. 15, 2016 (13 pages).
"Response to Non-Final Office Action," for U.S. Appl. No. 15/061,234, mailed Aug. 26, 2016 and filed with the USPTO Nov. 28, 2016 (8 pages).
"Final Office Action," for U.S. Appl. No. 14/063,113 dated Oct. 17, 2016 (19 pages).
"Non-Final Office Action," for U.S. Appl. No. 15/061,234 dated Aug. 26, 2016 (47 pages).
"Communication Pursuant to Rule 164(2)(b) and Article 94(3) EPC," for European Patent Application No. 14730319.2 dated Sep. 4, 2017 (12 pages).
"Office Action," for Japanese Patent Application No. 2015-539837 dated Aug. 31, 2017 (11 pages) with English translation.

* cited by examiner

APPARATUS AND METHODS FOR COATING MEDICAL DEVICES

This application is a continuation-in-part of U.S. patent application Ser. No. 13/906,599, filed May 31, 2013, which claims the benefit of U.S. Provisional Application No. 61/654,403, filed Jun. 1, 2012, and U.S. Provisional Application No. 61/661,684, filed Jun. 19, 2012. This application also claims the benefit of U.S. Provisional Application No. 61/820,223 filed May 7, 2013; U.S. Provisional Application No. 61/829,375, filed May 31, 2013; and U.S. Provisional Application No. 61/875,524, filed Sep. 9, 2013. The content of all of these applications are herein incorporated by reference in their entirety.

FIELD OF THE INVENTION

The present invention relates to apparatus and methods for coating medical devices.

BACKGROUND OF THE INVENTION

Functional improvements to implantable or insertable medical devices can be achieved by coating the surface of the device. For example, a coating formed on the surface of the device can provide improved lubricity, improved biocompatibility, or drug delivery properties to the surface. In turn, this can improve movement of the device in the body, extend the functional life of the device, or treat a medical condition near the site of implantation. However, various challenges exist for the design and use of coating apparatus designed to provide coatings to medical devices.

Traditional coating methods, such as dip coating, are often undesirable as they may result in flawed coatings that could compromise the function of the device or present problems during use. These methods can also result in coating inaccuracies, which can be manifested in variable amounts of the coated material being deposited on the surface of the device. When a drug is included in the coating material, it is often necessary to deliver precise amounts of the agent to the surface of the device to ensure that a subject receiving the coated device receives a proper dose of the agent. It has been difficult to achieve a great degree of accuracy using traditional coating methods and machines.

One type of insertable medical device is a balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guide wire, and manifold. A balloon catheter generally includes an elongated catheter shaft with an inflatable balloon attached to a distal section of the catheter shaft. At a proximal end of the catheter shaft, there is typically a manifold. At the manifold end, placement of the catheter can be facilitated using a guide wire. Guide wires are small and maneuverable when inserted into an artery. Once the guide wire is moved to the target location, the catheter with balloon portion is then fed over the guide wire until the balloon reaches the target location in the vessel. The balloon is typically inserted into the arterial lumen of a patient and advanced through the lumen in an unexpanded state. The balloon is then inflated when the catheter reaches target site resulting in application of mechanical force sufficient to cause vessel dilation. The balloon is typically inflated using a fluid, which is injected through an inflation port. The manifold can control the fluid introduction within shaft for expansion of the balloon. The mechanics of fluid transfer and introduction within balloons vary according to the specific design of the catheter, and are well known in the art.

SUMMARY OF THE INVENTION

Embodiments of the invention include apparatus and methods for coating drug coated medical devices. In an embodiment, the invention includes a coating apparatus including a coating application unit comprising a movement restriction structure; a fluid applicator; and an air nozzle. The apparatus can further include a rotation mechanism and a axial motion mechanism, the axial motion mechanism configured to cause movement of at least one of the coating application unit and the rotation mechanism with respect to one another.

In an embodiment, the invention includes a coating apparatus including a coating application unit comprising a fluid applicator; a fluid distribution bar; an air nozzle; and a rotation mechanism. The coating apparatus can further include an axial motion mechanism, the axial motion mechanism configured to cause movement of the coating application unit with respect to the rotator.

In an embodiment, the invention includes a method of coating including rotating a balloon catheter with a rotation mechanism, the balloon catheter comprising a balloon, contacting the balloon with a movement restriction structure defining a channel; applying a coating solution onto the surface of the balloon with a fluid applicator, contacting the surface of the balloon with a fluid distribution bar, blowing a stream of a gas onto the surface of the balloon, wherein the channel limits lateral movement of the balloon.

In an embodiment, the invention includes a coating apparatus. The coating apparatus can include a coating application unit. The coating application unit can include a fluid applicator having a lengthwise axis and a width. The fluid applicator can include a tip. The tip can include a face across the width of the fluid applicator. The face can be oriented at an angle of from about 15 to about 75 degrees with respect to the lengthwise axis of the fluid applicator. The fluid applicator can be configured to rotate around its lengthwise axis so as to change the orientation of the face with respect to the device being coated. The coating apparatus can further include a rotation mechanism and an axial motion mechanism. The axial motion mechanism can be configured to cause movement of at least one of the coating application unit and the rotation mechanism with respect to one another.

In an embodiment, the invention includes a method of coating a medical device. The method can include rotating a medical device to be coated with a rotation mechanism. The method can further include contacting the surface of the medical device with a fluid applicator having a lengthwise axis and a width. The fluid applicator can include a tip. The tip can include a face across the width of the fluid applicator. The face can be oriented at an angle of from about 15 to about 75 degrees with respect to the lengthwise axis of the fluid applicator. The method can include applying a coating solution onto the surface of the balloon with the fluid applicator. The method can further include rotating the fluid applicator about its lengthwise axis.

In an embodiment, the invention includes a coated medical device including a shaft, an expandable portion having a surface, and a coating disposed on the expandable portion. The coating can include a continuous coverage segment and a discontinuous coverage segment.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Embodiments herein can be used to apply visually uniform coatings, such as coatings including active agents, onto medical devices, such as onto the balloons of drug coated or drug eluting balloon catheters, that have substantially uniform active agent concentrations along the length of the medical device. For example, in some embodiments, coatings can be formed with apparatus and methods wherein each section of the device that has been coated contains an amount of the active agent that is within ten percent of the average amount of active agent across all sections coated.

Figure 1:
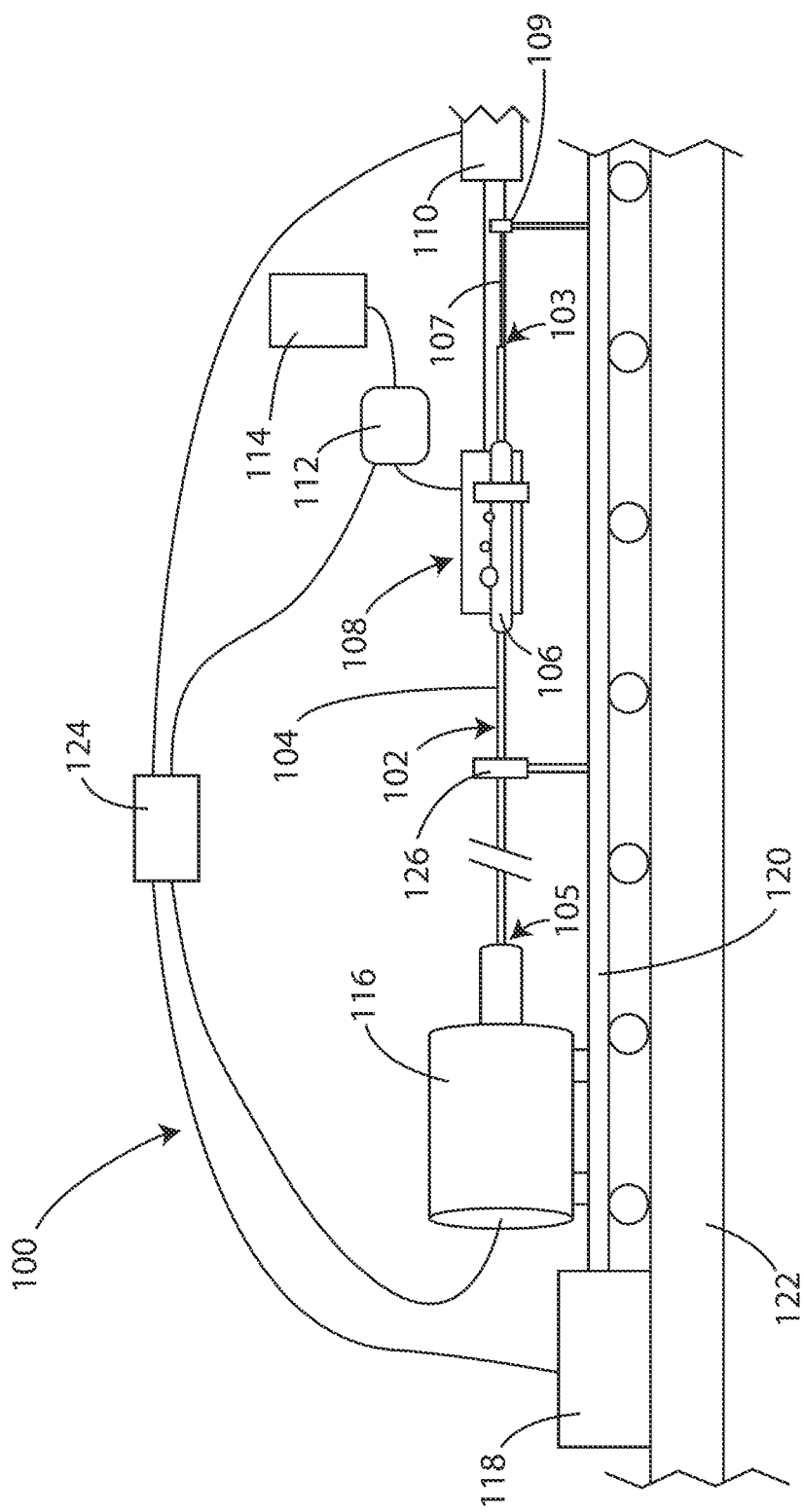
FIG. 1 is a schematic side view of a coating apparatus in accordance with various embodiments herein.

Referring now to FIG. 1, a schematic side view is shown of a coating apparatus 100 in accordance with various embodiments herein. The coating apparatus 100 is shown in conjunction with a drug coated balloon catheter 102. The drug coated balloon catheter 102 can include a catheter shaft 104 and a balloon 106. The balloon 106 can assume a deflated configuration and an inflated configuration. The drug coated balloon catheter 102 can include a distal end 103 and a proximal end 105. The drug coated balloon catheter 102 can include a proximal end manifold (not shown). The coating apparatus 100 can include a coating application unit 108. The coating apparatus 100 can further include, in some embodiments, an axial motion mechanism 110 (axial with respect to the axis of rotation of the balloon catheter and thus parallel to the lengthwise axis of the balloon catheter) that can function to move one or more components of the coating application unit 108. In some embodiments, axial motion can be substantially horizontal. In other embodiments, axial motion can be substantially vertical. In some embodiments, axial motion can be somewhere in between horizontal and vertical, depending on the orientation of the lengthwise axis of the balloon catheter. However, it will be appreciated that in other embodiments, the coating application unit 108 can remain stationary.

Coating of the balloon 106 to make it drug coated can occur starting at the proximal end of the balloon and proceeding to the distal end. However, in other embodiments, coating of the drug coated balloon 106 can occur starting at the distal end of the balloon and proceeding to the proximal end. In many embodiments, coating can take place with a single pass of the coating application unit 108 with respect to the balloon. However, in other embodiments, multiple passes of the coating application unit with respect to the balloon can be made.

The coating apparatus 100 can further include a fluid pump 112. The fluid pump 112 can be, for example, a syringe pump. The fluid pump 112 can be in fluid communication with components of the coating application unit 108 (such as the fluid applicator) and with a fluid reservoir 114. The fluid pump 112 can operate to pump a coating solution at a rate sufficient to apply about 0.5 µl to about 10 µl of the coating solution per millimeter of length of the balloon or other device to be coated. The coating apparatus 100 can further include a rotation mechanism 116 (or rotating balloon catheter fixture). The rotation mechanism 116 can be directly or indirectly coupled to the drug coated balloon catheter in order to rotate the drug coated balloon catheter 102 around its lengthwise (major) axis (about the central lumen of the catheter). In some embodiments, the drug coated balloon catheter can be rotated at a speed of between 100 and 400 rotations per minute. In some embodiments, the drug coated balloon catheter can be rotated at a speed of between 200 and 300 rotations per minute.

In some embodiments, a guide wire 107, passing through the central lumen of the catheter, can extend from the distal tip of the catheter and be inserted into a distal tip support ring 109 or guide. In this manner, the guide wire 107 can be used to support the distal tip of the balloon catheter to be coated while allowing the balloon catheter to rotate freely.

The coating apparatus 100 can further include, in some embodiments, an axial motion mechanism 118 which can be configured to move the drug coated balloon catheter 102 in the direction of its lengthwise major axis. In some embodiments, axial motion can be substantially horizontal. In other embodiments, axial motion can be substantially vertical. In some embodiments, axial motion can be somewhere in between horizontal and vertical, depending on the orientation of the lengthwise axis of the balloon catheter. In some embodiments, the axial motion mechanism 118 can be a linear actuator. In some embodiments, the axial motion mechanism 118 can include an electric motor. The coating apparatus 100 can further include a frame member 120 (in some embodiments this can also be referred to as an axial motion support rail). The frame member 120 can support other components of the coating apparatus 100 such as one or more guides 126. The frame member 120 can itself be support by a platform 122. The coating apparatus 100 can further include a controller 124 that can serve to control operation of the coating apparatus 100 including, specifically, fluid pump 112, axial motion mechanism 110, rotation mechanism 116, and axial motion mechanism 118.

Figure 2:
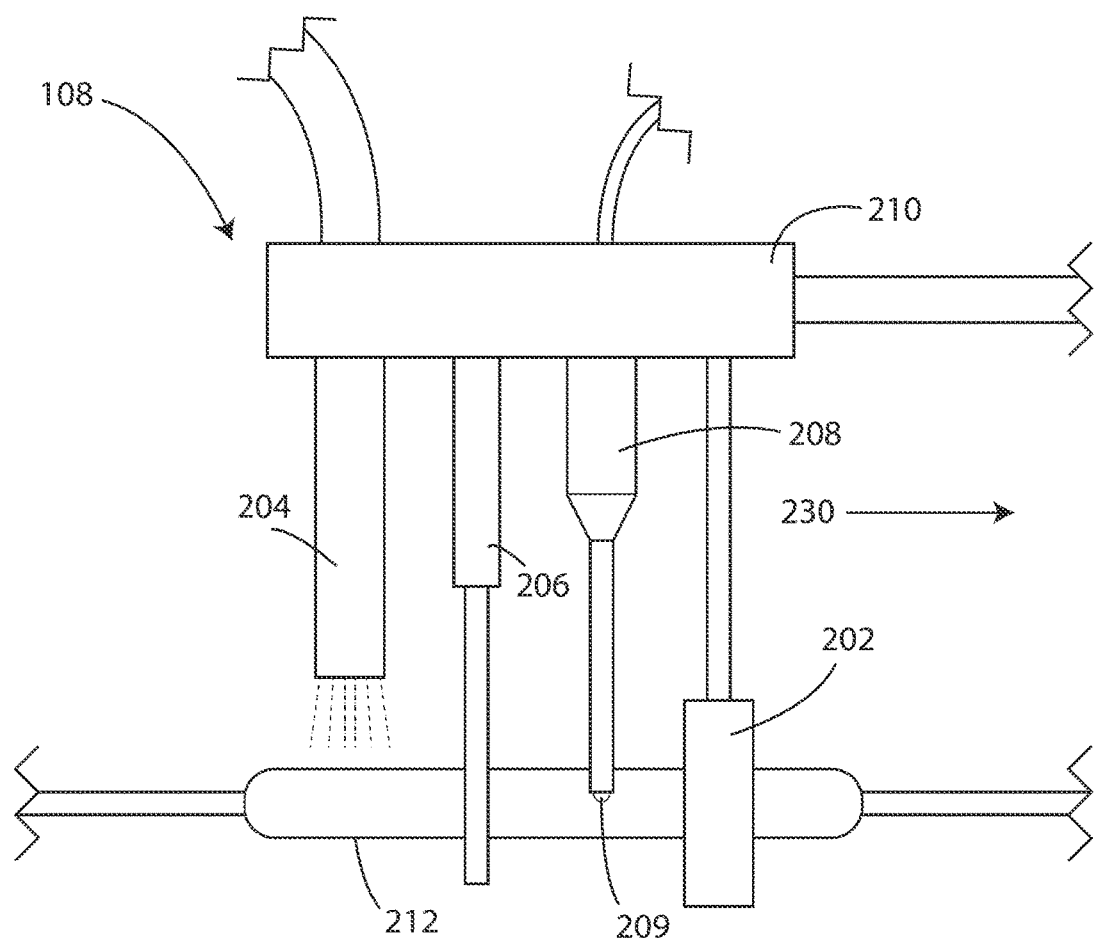
FIG. 2 is a schematic view of a coating application unit in accordance with various embodiments herein.

Referring now to FIG. 2, a schematic view of a coating application unit 108 in accordance with various embodiments herein is shown. The coating application unit 108 can include a movement restriction structure 202 (or wobble control structure), an air nozzle 204, a fluid distribution bar 206, and a fluid applicator 208. The movement restriction structure 202 can serve to limit the lateral motion (e.g., movement in a direction perpendicular to the lengthwise axis of the catheter) of the balloon during a coating operation.

The fluid applicator 208 can serve to apply a coating solution 209 to the surface of the balloon 212 on the drug coated balloon catheter. In some embodiments, the fluid applicator 208 is less than or equal to about 1 cm away from the movement restriction structure 202. In some embodiments, the air nozzle 204 is less than or equal to about 2 cm away from the fluid applicator 208. The air nozzle 204 can provide a stream of a gas in order to assist in drying the coating solution after it has been applied to the balloon or other medical device.

The fluid distribution bar 206 can serve to promote distribution of the applied coating solution. For example, the fluid distribution bar 206 can serve to prevent pooling of the applied coating solution. In some embodiments, the fluid distribution bar 206 can be at least about 0.5 mm away from the fluid applicator and less than 2 cm away. In some embodiments, the fluid distribution bar 206 can be at least about 0.2 cm away from the fluid applicator and less than 2 cm away.

In this embodiment, the coating application unit 108 can move, relative to the balloon 212 in the direction of arrow 230. As such, during a coating operation, the movement restriction structure 202 can pass over the balloon first, followed by the fluid applicator 208, followed by the fluid distribution bar 206, with the air nozzle last. It should be emphasized, however, that this movement is relative in the sense that in some embodiments the coating application unit 108 is moving and the balloon 212 is rotating but otherwise stationary, in some embodiments the balloon 212 is rotating and moving in the direction of its lengthwise axis and the coating application unit 108 is stationary, in still other embodiments both the coating application unit 108 and the balloon 212 are moving. The speed of movement of the balloon 212 relative to the coating application unit 108 can vary depending on the amount of coating solution to be applied. In some embodiments the speed can be from about 0.02 centimeters per second to about 0.2 centimeters per second.

It will be appreciated that based on the rotation of the drug coated balloon catheter and the movement of the balloon relative to the coating application unit that the path of the deposition of the coating onto the balloon follows a roughly helical path. It will be appreciated that the combination of the rotation speed of the drug coated balloon catheter and the speed of the movement of the balloon relative to the coating application unit can influence the amount of coating solution that is deposited at any given point and the nature of the helical path. For example, the coating material can be deposited in helical layers that partially overlap one another at their edges, helical layers wherein the edge of one turn substantially meets the edge of a previous turn, and helical layers wherein there are gaps in between subsequent helical turns. In some embodiments, these helical patterns can be configured so as to maximize release of the active agent. For example, in some embodiments, the apparatus can be used to coat device so as to produce helical ridges of the coating material on the balloon surface.

In some embodiments, the coating application unit 108 can optionally include a manifold block 210. The manifold block 210 can facilitate support of, and in some embodiments movement of, the components of the coating application unit 108. In some embodiments, the components of the coating application unit can move together as a unit during a coating operation. However, in other embodiments the components of the coating application unit are substantially separate from one another and can move independently. In some embodiments, the components of the coating application unit are all substantially stationary during a coating operation.

While the components of the coating application unit 108 are shown in FIG. 2 as being within a particular plane and disposed at approximately the same angle with respect to the balloon 212 being coated, it will be appreciated that this is not the case with all embodiments herein. In some embodiments, the components of the coating application unit 108 lie in different planes with respect to the balloon 212 and/or the components of the coating application unit 108 are disposed at different angles (both with respect to the lengthwise axis of the balloon and radially) with respect to the balloon.

Figure 3:
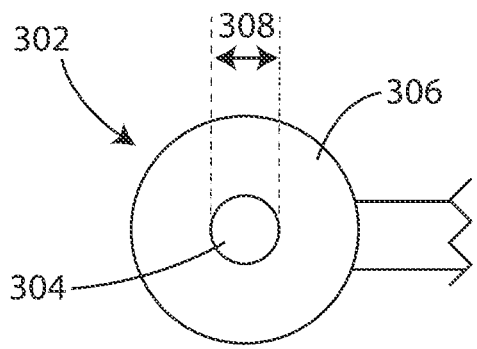
FIG. 3 is a schematic view of a movement restriction structure in accordance with various embodiments herein.

Referring now to FIG. 3, a schematic end view is shown of a movement restriction structure 302 in accordance with various embodiments herein. The structure 302 can include a body member 306 defining a channel 304 or aperture. The body member 306 can be formed of various materials such as polymers, metals, ceramics, and the like. In a particular embodiment, the body member 306 is formed of polytetrafluoroethylene (PTFE). The channel 304 can have a diameter 308 that is sufficiently large so as to accommodate the balloon of a drug coated balloon catheter in an expanded state. In the example of FIG. 3, the channel 304 is shown as being bounded in a radially continuous manner by the body member 306 (e.g., it is completely surrounded on all sides by the body member 306). However, it will be appreciated that in some embodiments the channel 304 is not bounded in a radially continuous manner by the body member 306.

Figure 4:
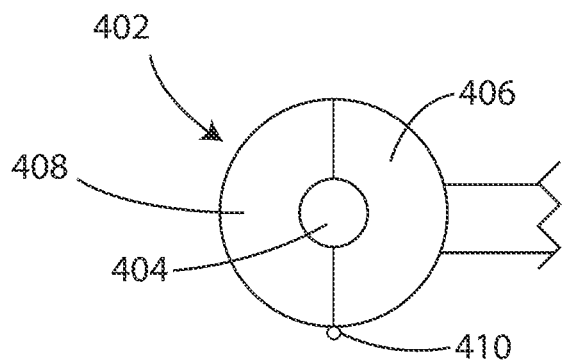
FIG. 4 is a schematic view of a movement restriction structure in accordance with various embodiments herein.

In some embodiments the movement restriction structure can include multiple pieces that together define a channel or aperture. Referring now to FIG. 4, a movement restriction structure 402 is shown including a body member that includes a first piece 406 and a second piece 408 that together define a channel 404 or aperture. The first piece 406 and second piece 408 are joined together by a hinge 410 in this embodiment, however it will be appreciated that there are many ways known to those of skill in the art by which to hold two structure pieces in association with one another.

Figure 5:
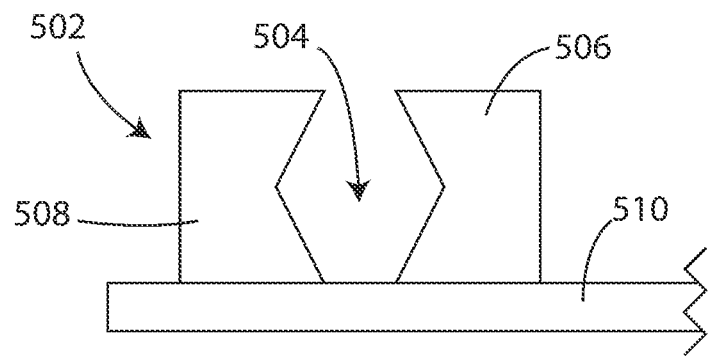
FIG. 5 is a schematic view of a movement restriction structure in accordance with various embodiments herein.

It will be appreciated that body members of movement restriction structures can take on many different shapes. In addition, the shape of the channel defined by the body member(s) can take on many different shapes. Referring now to FIG. 5, a movement restriction structure 502 is shown including a first side piece 506 and a second side piece 508 that together define a channel 504 or aperture. In this case, the first side piece 506 and the second side piece 508 are supported by a frame member 510. However, it will be appreciated that there are many different ways of supporting the first side piece 506 and the second side piece 508. In some embodiments, one or both of the first side piece 506 and the second side piece 508 can be spring loaded such that it is biased toward sliding inward toward the other piece. In other embodiments, one or both of the first side piece 506 and the second side piece 508 can be adjustable and then fixed in position so as to create a channel 504 of a desired size.

Figure 6:
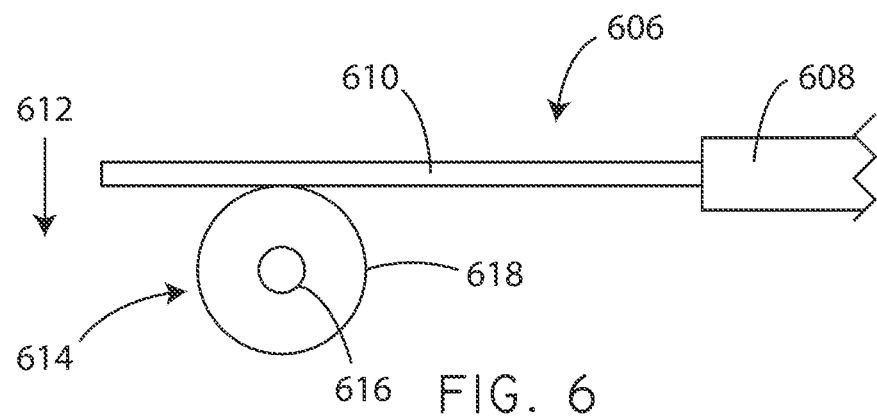
FIG. 6 is a schematic end view of a fluid distribution bar in conjunction with the balloon of a balloon catheter.

Referring now to FIG. 6 a schematic end view of a fluid distribution bar 606 in conjunction with the balloon 618 of a drug coated balloon catheter 614 is shown. In some embodiments, the fluid distribution bar 606 can include a support structure 608 and a shaft 610. In some embodiments, the support structure 608 can be omitted. The shaft 610 can be formed of various materials such as polymers, metals, ceramics, and the like. In a particular embodiment, the shaft 610 is formed of polytetrafluoroethylene (PTFE). The shaft 610 can be of various lengths and diameters and can have various cross-sectional shapes. In some embodiments, the shaft 610 is from about 2 mm to about 15 cm and is substantially circular in cross-sectional shape. In some embodiments, the shaft is about 1/16 inch in diameter. The shaft 610 is configured to rest against the balloon 618 of the balloon catheter 614.

In yet other embodiments the fluid distribution bar 606 can include multiple rods or extensions from support structure 608. Exemplary of these embodiments can include, but are not limited to, a comb-like structure or a brush.

The balloon 618 is supported by the catheter shaft 616, but generally only at the ends of the balloon 618. Because of the limited support of the balloon 618 by the catheter shaft 616, the inherent flexibility of the balloon material and manufacturing variations, the balloon 618 may not be perfectly round. As such, when it is being rotated during a coating operation there may be variations in the distance of the outer surface of the balloon 618 from the catheter shaft 616 of the balloon catheter 614. If unaccounted for, this could lead to circumstances where the fluid distribution bar 606 does not maintain contact with the surface of the balloon 618. As such, the shaft 610 of the fluid distribution bar 606 can be configured to maintain contact with the surface of the balloon 618. For example, the shaft 610 of the fluid distribution bar 606 can be positioned such that it exerts a small degree of pressure against the surface of the balloon 618 such that when an irregularity in the balloon is encountered the fluid distribution bar 606 can move slightly in order to maintain contact with the balloon surface. In some embodiments the shaft 610 of the fluid distribution bar 606 is flexible to accommodate movement to stay in contact with the balloon surface. In other embodiments, the fluid distribution bar 606 can be configured to pivot from where it is mounted in order to accommodate movement to stay in contact with the balloon surface.

While the shaft 610 of the fluid distribution bar 606 is shown in FIG. 6 as contacting the top of the balloon 618 and thus exerting a pressure downward in the direction of arrow 612, it will be appreciated that in other embodiments the surface of the balloon 618 can be contacted at other points along its surface, such as on the sides or on the bottom.

Figure 7:
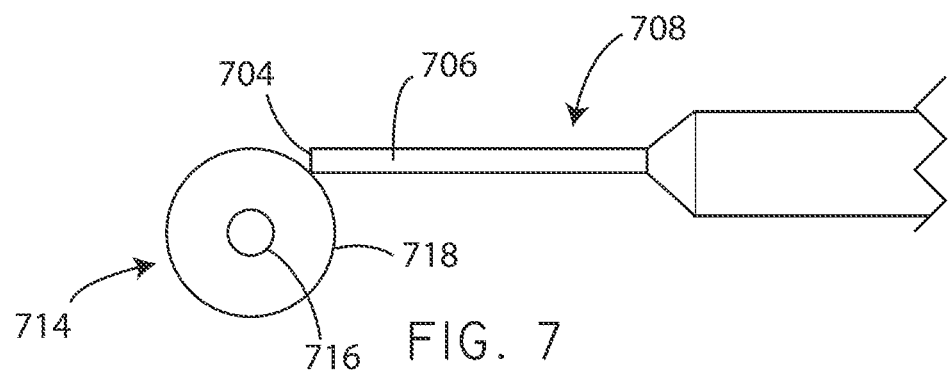
FIG. 7 is a schematic end view of a fluid applicator in conjunction with the balloon of a balloon catheter.

Referring now to FIG. 7, a schematic end view of a fluid applicator 708 in conjunction with the balloon 718 of a drug coated balloon catheter 714 is shown in accordance with an embodiment of the invention. The fluid applicator 708 can include a shaft 706 and an orifice 704. In some embodiments, the fluid applicator 708 can be a pipette. Fluid, such as a coating solution, can travel through the shaft 706 of the fluid applicator 708 in order to be deposited on the surface of the balloon 718 of the drug coated balloon catheter 714. The shaft 706 is configured to rest against the balloon 718 of the balloon catheter 714. The balloon 718 is supported by the catheter shaft 716, but generally only at the ends of the balloon 718. Because of the limited support of the balloon 718 by the catheter shaft 716, the inherent flexibility of the balloon material and manufacturing variations, the balloon 718 may not be perfectly round. As such, when it is being rotated during a coating operation there may be variations in the distance of the outer surface of the balloon 718 from the catheter shaft 716 of the balloon catheter 714. If unaccounted for, this could lead to circumstances where the fluid applicator 708 does not maintain contact with the surface of the balloon 718. As such, the shaft 706 of the fluid applicator 708 can be configured to maintain contact with the surface of the balloon 718. For example, the shaft 706 of the fluid applicator 708 can be positioned such that it exerts a small degree of pressure against the surface of the balloon 718 such that when an irregularity in the balloon 718 is encountered the fluid applicator 708 can move slightly in order to maintain contact with the balloon surface. In some embodiments the shaft 706 of the fluid applicator 708 is flexible to accommodate movement to stay in contact with the balloon surface. In other embodiments, the fluid applicator 708 can be configured to pivot from where it is mounted in order to accommodate movement to stay in contact with the balloon surface. In other embodiments, the fluid applicator may not be in direct contact with the balloon surface but situated closely, for example within 1 millimeter.

While the shaft 706 of the fluid applicator 708 is shown in FIG. 7 as contacting the upper right side (approximately equivalent to an area between the 1 and 2 position of a clock face) of the balloon 718, it will be appreciated that in other embodiments the surface of the balloon 718 can be contacted at other points along its surface. For example, in some embodiments, the very top of the balloon 718 can be contacted by the fluid applicator 708.

In some embodiments the fluid distribution bar 606 and the fluid applicator 708 can be configured such that the shaft 610 of the fluid distribution bar 606 contacts the surface of the balloon at approximately the same point radially along the surface of the balloon as the shaft 706 of the fluid applicator 708. In some embodiments, the fluid distribution bar 606 and the fluid applicator 708 can be configured such that the shaft 610 of the fluid distribution bar 606 contacts the surface of the balloon within at least 90 degrees radially along the surface of the balloon as the shaft 706 of the fluid applicator 708.

Figure 8:
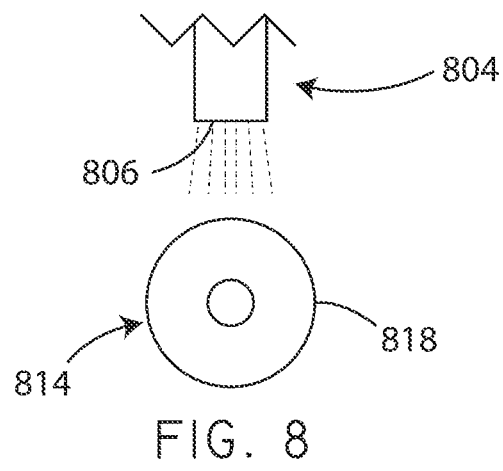
FIG. 8 is a schematic end view of an air nozzle in conjunction with the balloon of a balloon catheter.

Referring now to FIG. 8, a schematic end view of an air nozzle 804 in conjunction with the balloon 818 of a drug coated balloon catheter 814 is shown. The air nozzle 804 can include an orifice 806. A gas such nitrogen, ambient air or another gas can be directed to flow out of the orifice 806 and towards the balloon 818 of the drug coated balloon catheter 814. In some embodiments, the gas can be heated. For example, in some embodiments the gas can be from about 50 to about 70 degrees Celsius. While the orifice 806 of the air nozzle 804 is shown in FIG. 8 as directing air to the top of the balloon 818, it will be appreciated that in other embodiments the air nozzle 804 and orifice 806 can be configured to direct air at other parts of the balloon 818 such as, but not limited to, the sides or the bottom.

Figure 9:
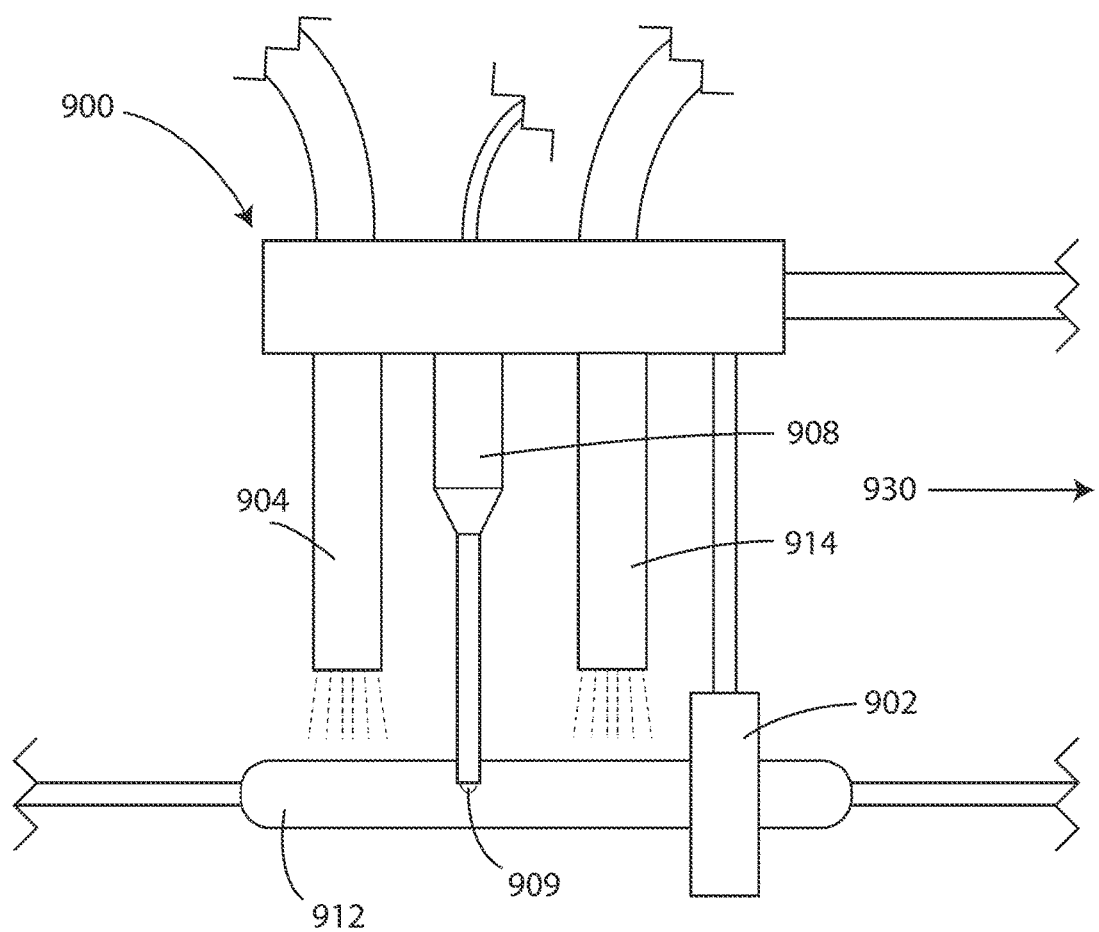
FIG. 9 is a schematic view of a coating application unit in accordance with various embodiments herein.

Referring now to FIG. 9, a schematic view of a coating application unit in accordance with various embodiments herein is shown. The coating application unit 900 can include a movement restriction structure 902, a first air nozzle 914, a fluid applicator 908, and a second air nozzle 904. The first air nozzle 914 is disposed on one side of the fluid applicator 908 and the second air nozzle 904 is disposed on the other side of the fluid applicator 908. In some embodiments the first air nozzle 914 can act to avoid pooling of the coating at the fluid applicator 908. In some embodiments the second air nozzle 904 can act to avoid pooling of the coating fluid at the fluid applicator 908. The fluid applicator 908 can serve to apply a coating solution 909 to the surface of the balloon on the drug coated balloon catheter. Other embodiments can include three or more air nozzles.

In this embodiment, the coating application unit 900 can move, relative to the balloon 912 in the direction of arrow 930. As such, during a coating operation, the movement restriction structure 902 can pass over the balloon first. It should be emphasized, however, that this movement is relative in the sense that in some embodiments the coating application unit 900 is moving and the balloon 912 is rotating but otherwise stationary, in some embodiments the balloon 912 is rotating and moving in the direction of its lengthwise axis and the coating application unit 900 is stationary, in still other embodiments both the coating application unit 900 and the balloon 912 are moving.

Figure 10:
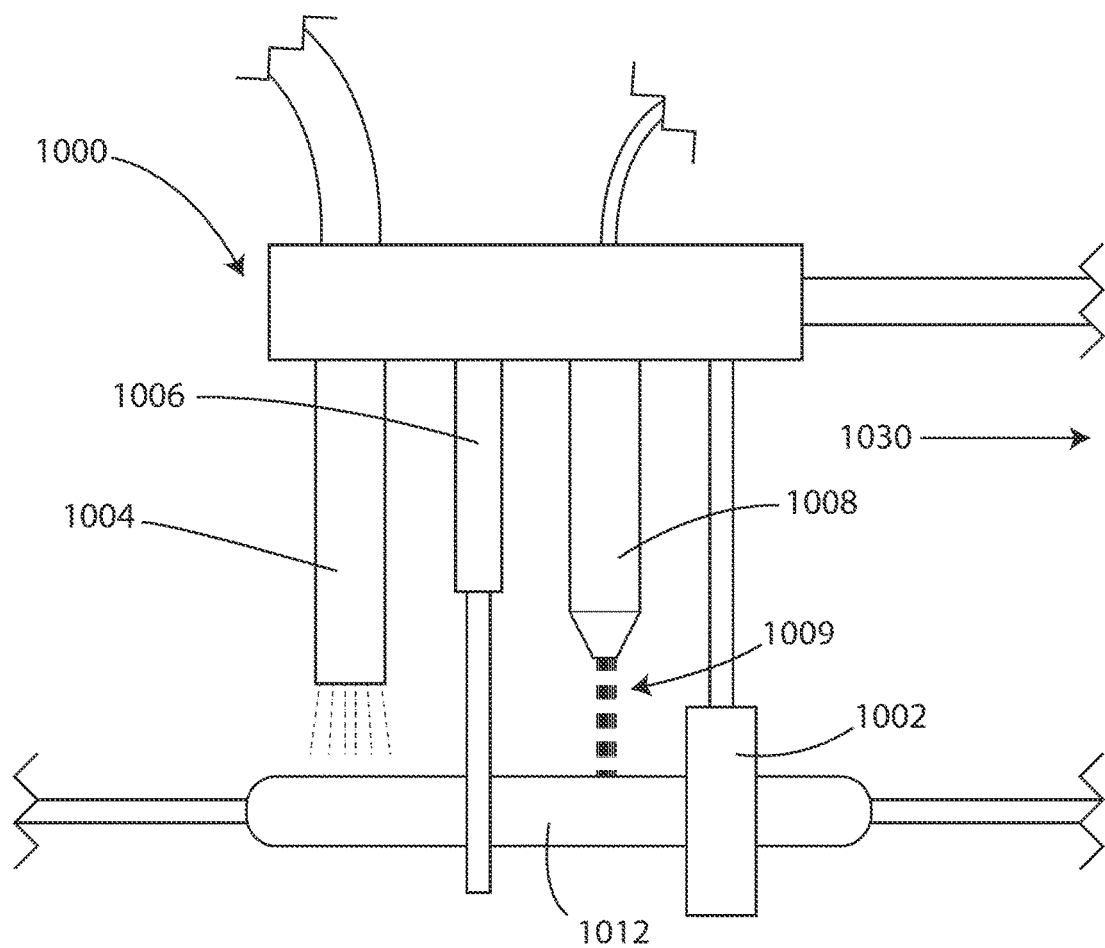
FIG. 10 is a schematic view of a coating application unit in accordance with various embodiments herein.

It will be appreciated that the coating solution can be applied on to the balloon in various ways including, but not limited to, spraying (including both ultrasonic spraying and conventional spraying techniques), dribbling, blade coating, contact printing, drop coating, or the like. In some embodiments, the fluid applicator can include a fluid spray nozzle. Referring now to FIG. 10, a schematic view of a coating application unit in accordance with various embodiments herein is shown. The coating application unit 1000 can include a movement restriction structure 1002, an air nozzle 1004, a fluid distribution bar 1006, and a fluid spray nozzle 1008. The fluid spray nozzle 1008 can serve to apply a coating solution 1009 to the surface of the balloon 1012 on the drug coated balloon catheter. In some embodiments there is a small gap between the fluid spray nozzle 1008 and the balloon 1012. For example, the gap can be between 1 millimeter and 10 centimeters. In some embodiments, multiple fluid applicators and/or spray nozzles can be used.

In this embodiment, the coating application unit 1000 can move, relative to the balloon 1012 in the direction of arrow 1030. As such, during a coating operation, the movement restriction structure 1002 can pass over the balloon first. It should be emphasized, however, that this movement is relative in the sense that in some embodiments the coating application unit 1000 is moving and the balloon 1012 is rotating but otherwise stationary, in some embodiments the balloon 1012 is rotating and moving in the direction of its lengthwise axis and the coating application unit 1000 is stationary, in still other embodiments both the coating application unit 1000 and the balloon 1012 are moving.

Figure 11:
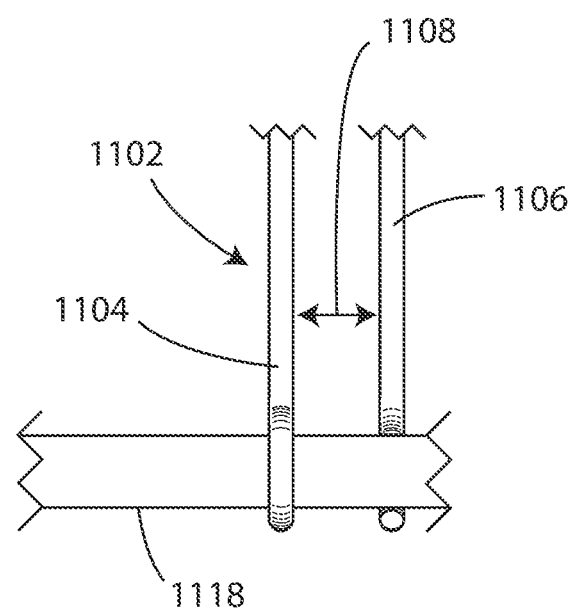
FIG. 11 is a schematic top view of a movement restriction structure in accordance with various embodiments herein.

FIG. 11 is a schematic top view of a movement restriction structure in accordance with various embodiments herein. The structure 1102 can include a first body member 1104 and a second body member 1106. The first and second body members 1104, 1106 can be formed of various materials such as polymers, metals, ceramics, and the like. The first and second body members 1104, 1106 can function together to restrict movement of a balloon 1118 to be coated. The first and second body members 1104, 1106 can be separated from one another by a distance 1108 that is greater than or equal to the diameter of the balloon 1118. In some embodiments, the distance 1108 is approximately equal to the balloon 1118. In some embodiments, the distance 1108 is between about 3 millimeters and about 10 millimeters.

Figure 12:
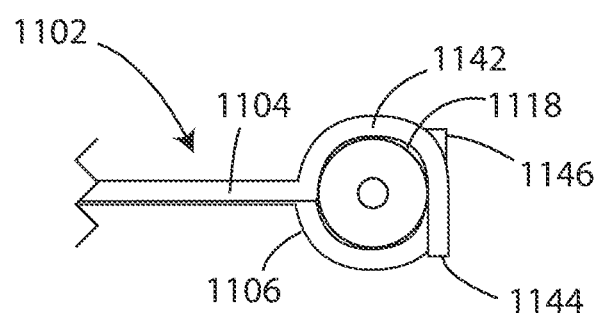
FIG. 12 is a schematic end view of a movement restriction structure in accordance with various embodiments herein.
Figure 13:
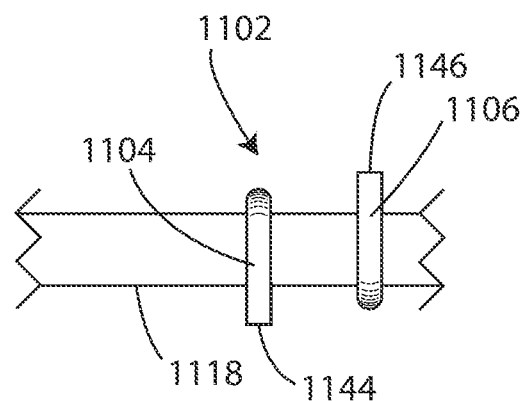
FIG. 13 is a schematic front view of a movement restriction structure in accordance with various embodiments herein.

FIG. 12 is a schematic end view of the movement restriction structure 1102. The first body member 1104 can include a curved segment 1142 and an end 1144. The curved segment 1142 can define a portion of a channel which can surround at least a portion of the balloon 1118, thereby restricting its movement. In some embodiments, the second body member 1106 can be formed similarly but with a different orientation so that together the first body member 1104 and the second body member 1106 can effectively restrict movement of the balloon 1118. For example, the end 1146 of the second body member 1106 can be pointed upward instead of downward. FIG. 13 is a schematic front view of the movement restriction structure 1102 that shows the differing orientations of the first body member 1104 and the second body member 1106.

Figure 14:
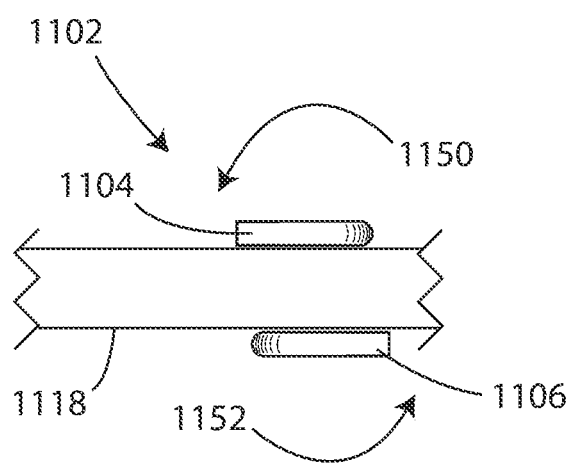
FIG. 14 is a schematic front view of a movement restriction structure in accordance with various embodiments herein.

It will be appreciated that the balloon can be loaded into the movement restriction structure in various ways. For example, in some embodiments, the balloon catheter can simply be threaded through the movement restriction structure before or after being connected with other portions of the apparatus in preparation for coating. In other embodiments, the movement restriction structure itself can be manipulated in order to load the balloon. For example, in some embodiments, the movement restriction structure can be rotated into an open orientation in order to accommodate loading the balloon from the side. Then, in some embodiments, the movement restriction structure can be rotated from the open orientation to a closed orientation in order to lock the balloon in place. Referring now to FIG. 14, a schematic front view of the movement restriction structure 1102 is shown illustrating an open orientation. In this view, it can be seen that the first body member 1104 and the second body member 1106 are rotated approximately 90 degrees from their respective positions in FIG. 13. The balloon 1118 can be slid out from between the first and second body members 1104, 1106 when the movement restriction structure 1102 is in this orientation. In operation, then, a new balloon to be coated can be slid back in between the first and second body members 1104, 1106 and then the body members can be rotated in the direction of arrows 1150 and 1152 to put the movement restriction structure 1102 into the closed position (illustrated in FIG. 13) where the balloon 1118 is locked in place. In some embodiments, the first and second body members 1104, 1106 can be rotated in either direction. The first and second body members 1104, 1106 can be rotated together around a single axis or independently from one another around two separate axes.

Figure 15:
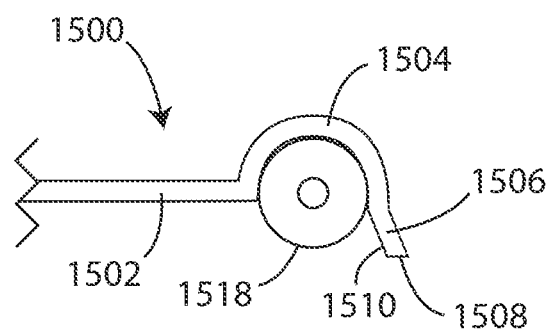
FIG. 15 is a schematic end view of a movement restriction structure in accordance with various embodiments herein.

It will be appreciated that body members of movement restrictions structures in accordance with embodiments herein can also include various other features. Referring now to FIG. 15, a schematic end view of portions of a movement restriction structure 1500 are shown in accordance with various embodiments herein. The movement restriction structure 1500 can include a first body member 1502. The first body member 1502 can include a curved segment 1504 and an end 1508. The curved segment 1504 can define a portion of a channel which can surround at least a portion of the balloon 1518, thereby restricting the balloon's 1518 movement, in conjunction with a second body member (not shown in this view). The first body member 1502 can also include an alignment lip 1506 adjacent to the end 1508. The alignment lip 1506 can include a surface 1510 that is angled away from the channel defined by the curved segment 1504. The alignment lip 1506 can aid in positioning the balloon 1518 within the channel formed by the curved segment 1504. For example, when the first body member 1502 is rotated starting from the open position, if the balloon 1518 is slightly out of position by being too close to the end 1508, the surface 1510 of the alignment lip 1506 will contact the balloon 1518 surface and cause the balloon 1518 to move into alignment with the channel.

Figure 16:
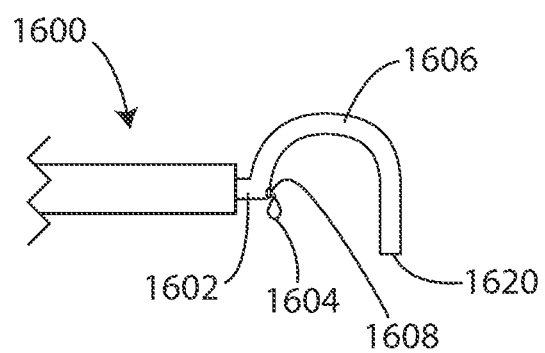
FIG. 16 is a schematic end view of a fluid applicator in accordance with various embodiments herein.

It will be appreciated that fluid applicators can take on various configurations in accordance with embodiments herein. FIG. 16 is a schematic end view of a fluid applicator 1600 in accordance with various embodiments herein. The fluid applicator 1600 can include a shaft 1602 and an orifice 1608. The orifice 1608 can be located along the shaft 1602 at a position other than at the distal end 1620 of the shaft 1602. Fluid 1604, such as a coating solution, can pass from the fluid applicator 1600 through the orifice 1608 in order to be deposited on the surface of the balloon. The segment 1606 of the shaft 1602 that extends beyond where the orifice 1608 is located can be curved, in some embodiments, in order to form part of a channel which can serve to maintain the position of the balloon relative to the fluid applicator 1600. In some embodiments, segment 1606 can be disposed between the orifice 1608 and the distal end 1620 of the shaft 1602.

Figure 17:
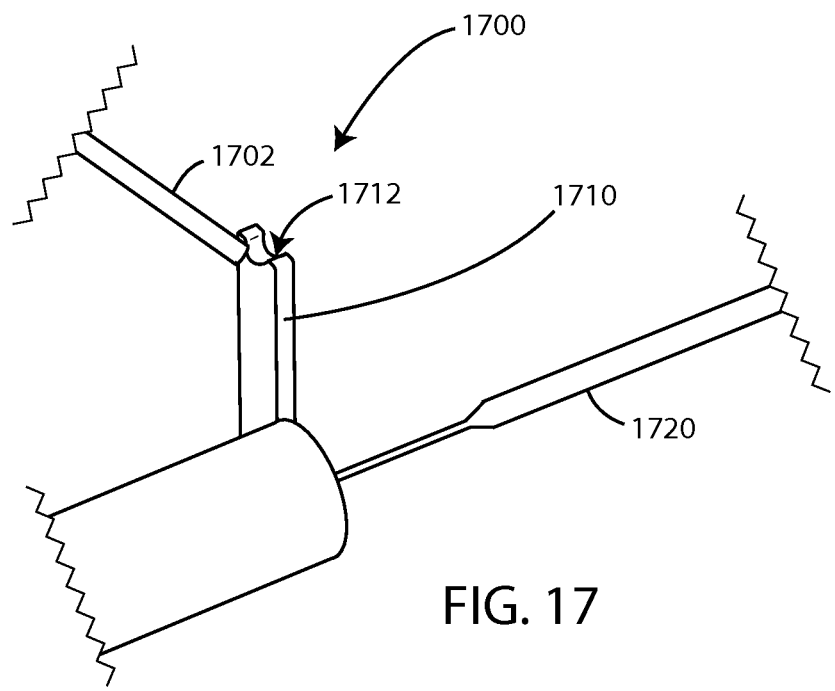
FIG. 17 is a schematic perspective view of a coating apparatus in accordance with various embodiments herein.

Referring now to FIG. 17, a schematic perspective view of a coating apparatus 1700 is shown in accordance with various embodiments herein. The coating apparatus 1700 can include a fluid applicator 1702 and a movement restriction structure 1710. The movement restriction structure 1710 can include an engagement surface 1712 having a U-shaped contour. A device to be coated, such as a balloon catheter 1720, is shown as ready for insertion into the movement restriction structure 1710.

Figure 18:
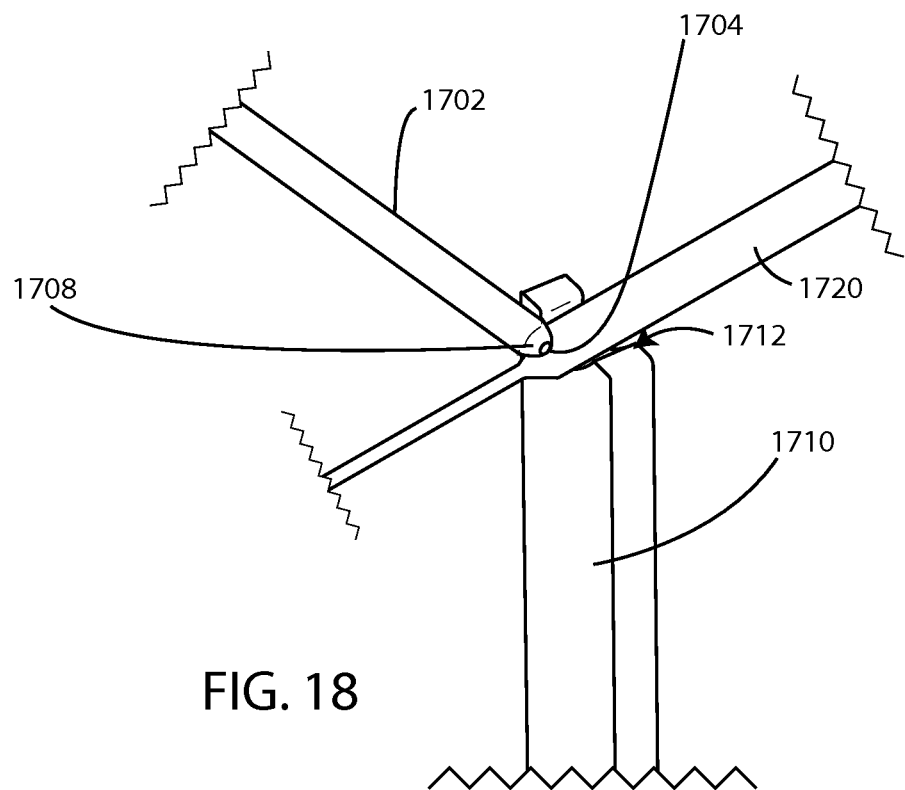
FIG. 18 is a schematic perspective view of a fluid applicator interfacing with balloon catheter as held by a movement restriction structure.
Figure 19:
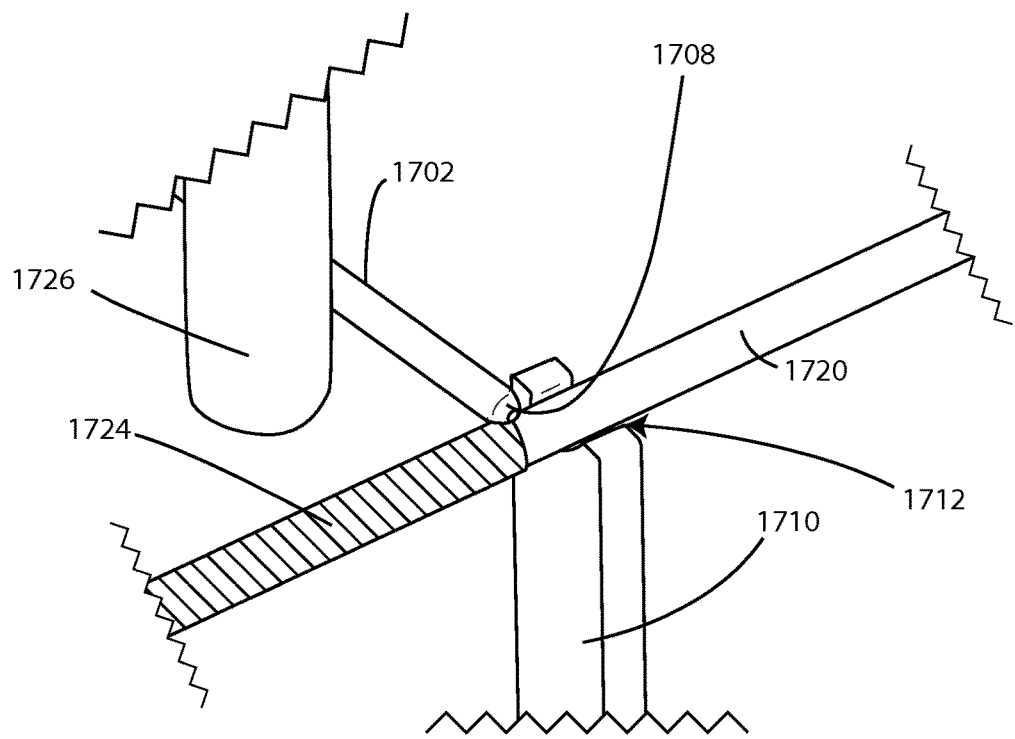
FIG. 19 is a schematic perspective view of a fluid applicator interfacing with balloon catheter as held by a movement restriction structure.

Referring now to FIG. 18, a schematic perspective view is shown of a fluid applicator 1702 interfacing with balloon catheter 1720 as held by a movement restriction structure 1710. The movement restriction structure 1710 can include an engagement surface 1712 having a U-shaped contour. The fluid applicator 1702 can include a contact surface 1708 that is angled with respect to the lengthwise axis of the fluid applicator 1702. The contact surface 1708 can fit against the balloon catheter during the coating operation so as to make contact and aid in holding the balloon catheter against the engagement surface 1712 of the movement restriction structure. 19 is a schematic perspective view of a fluid applicator 1702 interfacing with balloon catheter 1720 as held by a movement restriction structure 1710. A fluid coating composition 1722 is applied onto the surface of the balloon catheter 1720. The fluid coating composition 1722 then passes past a drying nozzle 1726 forming a dried coating 1724.

Figure 20:
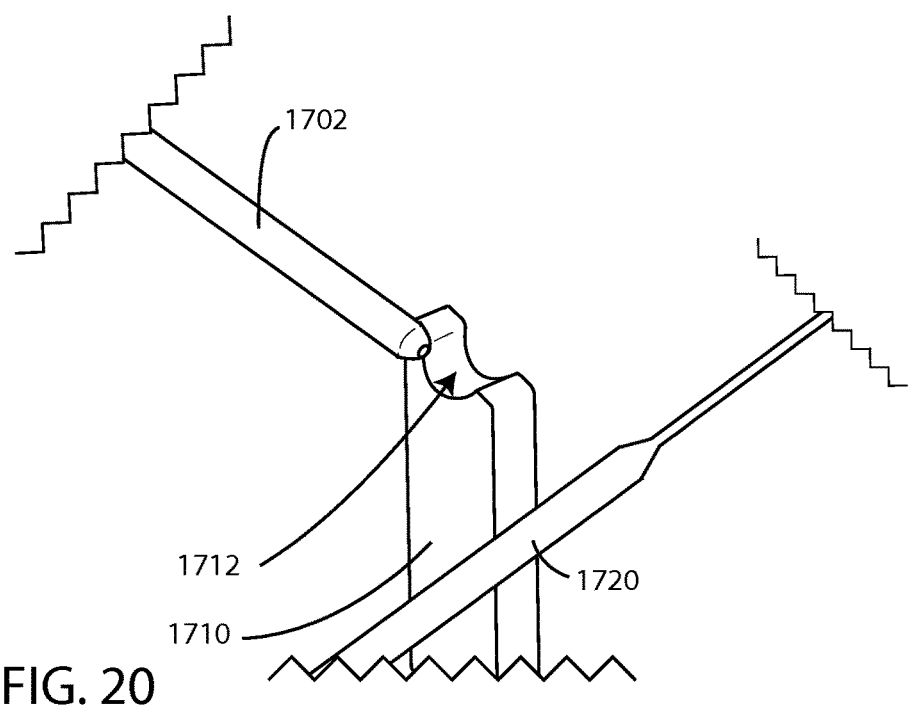
FIG. 20 is a schematic perspective view of elements of a coating apparatus in accordance with various embodiments herein.

Referring now to FIG. 20, a schematic perspective view of elements of a coating apparatus in accordance with various embodiments herein. In this view, a coating operation has been completed and the now coated balloon catheter 1720 has been removed from contact with the fluid applicator 1702 and has been moved out from within the engagement surface 1712 of the movement restriction structure 1710.

Figure 21:
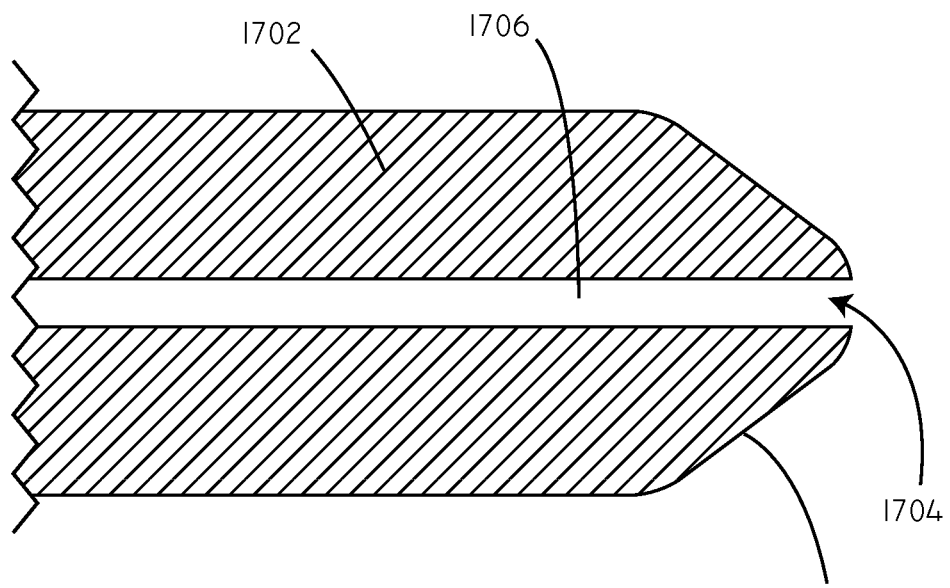
FIG. 21 is a schematic view through the middle of a fluid applicator in accordance with various embodiments herein.

Referring now to FIG. 21, a schematic cross-sectional view through the middle of a fluid applicator 1702 is shown in accordance with various embodiments herein. The fluid applicator 1702 can be formed of various materials including polymers, metals, ceramics, glasses, and the like. The fluid applicator 1702 can define a central channel 1706 through which a fluid coating composition can be delivered. The fluid applicator 1702 can further include a contact surface 1708. The contact surface 1708 can be angled with respect to the lengthwise axis of the fluid applicator 1702. In some embodiments, the contact surface 1708 can be angled from about 20 degrees to about 70 degrees with respect to the lengthwise axis of the fluid applicator 1702. In some embodiments, the contact surface 1708 is angled such that its surface is substantially parallel with a line that is a tangent to the balloon catheter 1720 at the point of contact between the fluid applicator 1702 and the balloon catheter 1720. A fluid orifice 1704 can be disposed as the distal end of the fluid applicator 1702.

Figure 22:
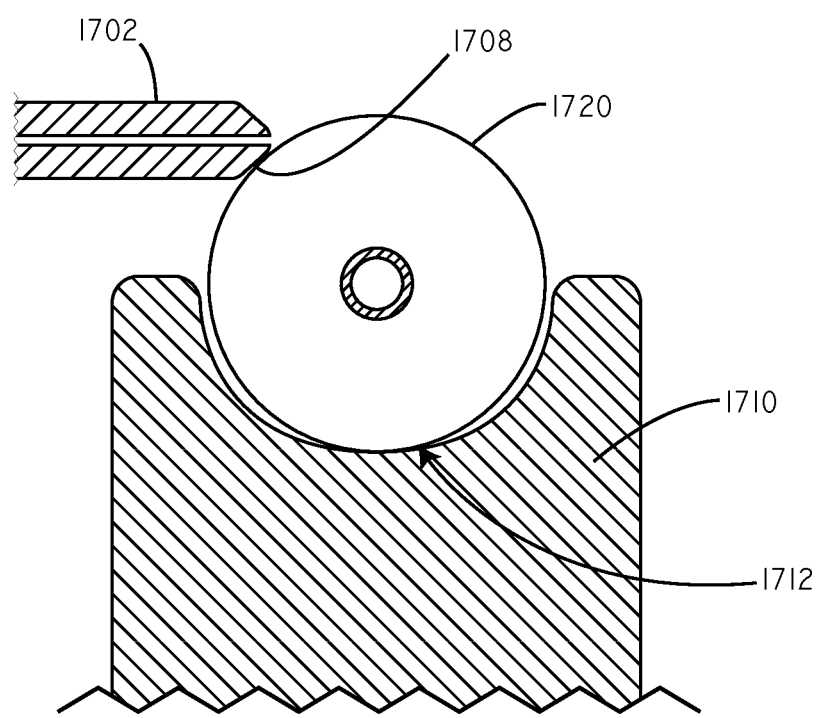
FIG. 22 is a schematic cross-sectional view of a fluid applicator interfacing with balloon catheter as held by a movement restriction structure.

FIG. 22 is a schematic cross-sectional view of a fluid applicator 1702 interfacing with a balloon catheter 1720 as held by a movement restriction structure 1710. The contact surface 1708 of the fluid applicator 1702 can contact the surface of the balloon catheter 1720. In some embodiments, the contact point between the fluid applicator 1702 and the surface of the balloon catheter 1720 can be at a position equivalent to between 9 and 12 on the face of a standard clock (or between 12 and 3 if the fluid applicator 1702 is arranged on the other side of the balloon catheter). If the position of 3 on a clock face is taken as 0 degrees, then the contact point can be between 180 degrees and 270 degrees (or between 270 degrees and 360 degrees if the fluid applicator 1702 is arranged on the other side of the balloon catheter). The surface of the balloon catheter 1720 can contact the engagement surface 1712 of the movement restriction structure 1710. In some embodiments, the leading and trailing edges of the engagement surface 1712 can include curved edges. In some embodiments, the engagement surface 1712 can include a radius of curvature extending from the leading edge to the trailing edge such that the point of contact with the surface of the balloon catheter is in the middle of the engagement surface between the leading edge and the trailing edge.

Figure 22A:
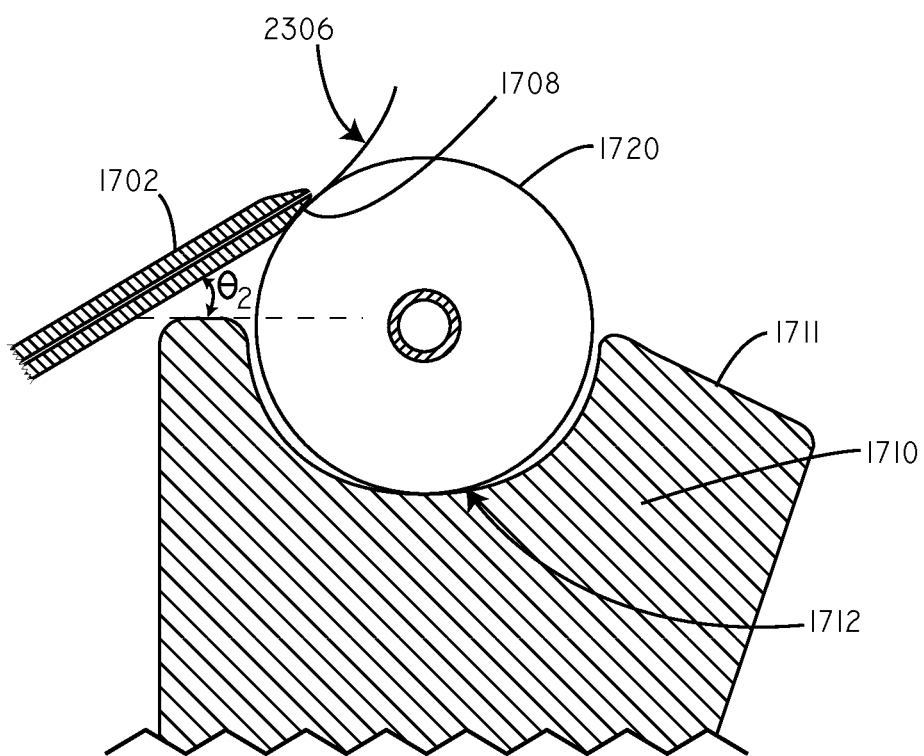
FIG. 22A is a schematic cross-sectional view of a fluid applicator interfacing with balloon catheter as held by a movement restriction structure in accordance with various embodiments.

FIG. 22A is a schematic cross-sectional view of a fluid applicator 1702 interfacing with a balloon catheter 1720 as held by a movement restriction structure 1710. The contact surface 1708 of the fluid applicator 1702 can contact the surface of the balloon catheter 1720. In some embodiments, the contact point between the fluid applicator 1702 and the surface of the balloon catheter 1720 can be at a position equivalent to between 9 and 12 on the face of a standard clock (or between 12 and 3 if the fluid applicator 1702 is arranged on the other side of the balloon catheter). If the position of 3 on a clock face is taken as 0 degrees, then the contact point can be between 180 degrees and 270 degrees (or between 270 degrees and 360 degrees if the fluid applicator 1702 is arranged on the other side of the balloon catheter). Additionally, the fluid applicator 1702 can be held at an angle $\theta_2$ (with respect to a fully horizontal position) from the contact points described above. The angle $\theta_2$ can vary between 0 (as shown in FIG. 22A) and as much as 30 degrees. The surface of the balloon catheter 1720 can contact the engagement surface 1712 of the movement restriction structure 1710. In some embodiments, the leading and trailing edges (e.g., oriented such that a line connecting the leading and trailing edges would be perpendicular to the cross-section of FIG. 22A and thus go into and out of the page) of the engagement surface 1712 can include curved edges. In yet other embodiments the engagement surface can include an engagement ramp 1711 to allow the balloon catheter 1720 to more easily become engaged with the engagement surface 1712. In some embodiments, the engagement surface 1712 can include a radius of curvature extending from the leading edge to the trailing edge such that the point of contact with the surface of the balloon catheter is in the middle of the engagement surface between the leading edge and the trailing edge.

In some embodiments the fluid distribution bar 2306 can act to further restrict movement and keep the balloon catheter 1720 engaged against the engagement surface 1712. In some exemplary embodiments, wherein the angle $\theta_2$ exceeds 15 degrees, the fluid distribution bar 2306 can further restrict movement and keep the balloon catheter 1720 engaged against the engagement surface 1712.

Figure 23:
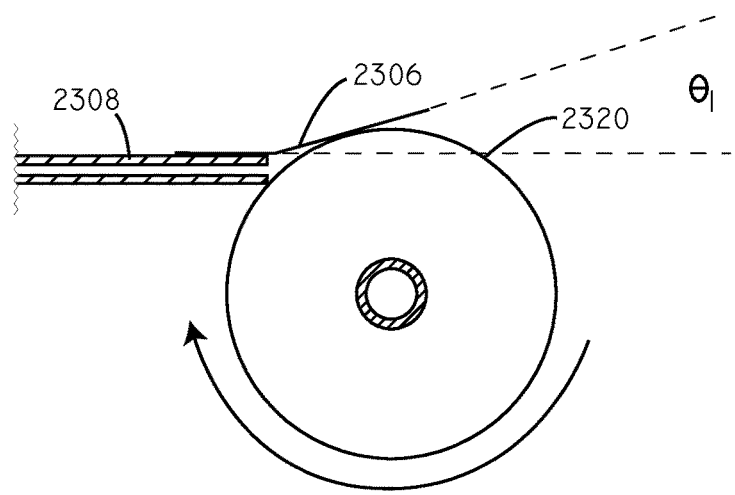
FIG. 23 is a schematic cross-sectional view of a fluid applicator interfacing with a balloon catheter in accordance with various embodiments

Referring now to FIG. 23, a schematic cross-sectional view is shown of a fluid applicator 2308 interfacing with the surface 2320 of a balloon catheter. The coating apparatus can further include a fluid distribution bar 2306 (or wire) that is connected to the fluid applicator 2308 and is arranged to contact the surface 2320 of the balloon catheter.

In this view, the fluid distribution bar 2306 is angled upward with respect to device to be coated such that it contacts the device to be coated at a higher point than the fluid applicator. In some embodiments, the fluid distribution bar is arranged such that it does not actually contact the surface of the device to be coated but is sufficiently close so as to contact any coating material that is deposited thereon. The angle ($\theta_1$) of the body of the fluid distribution bar 2306 with respect to the lengthwise major axis of the fluid applicator 2308 and/or the tip of the fluid applicator 2308 can be from about 0 degrees to about 20 degrees. In some embodiments the angle ($\theta_1$) is from about 0.5 degrees to about 20 degrees. In some embodiments, the angle is sufficient such that the body of the fluid distribution bar 2306 is tangent with respect to the surface of the device to be coated. In other embodiments, the fluid distribution bar is not be angled upward.

Figure 24:
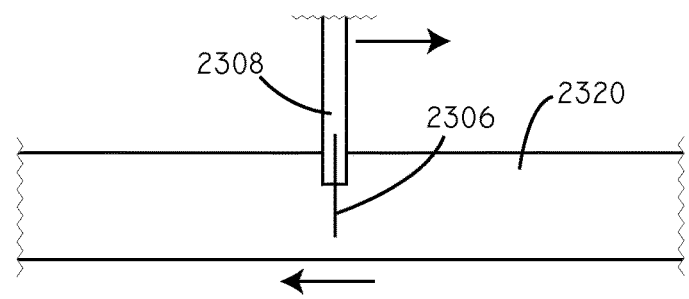
FIG. 24 is a schematic top view of a fluid applicator interfacing with a balloon catheter in accordance with various embodiments.
Figure 25:
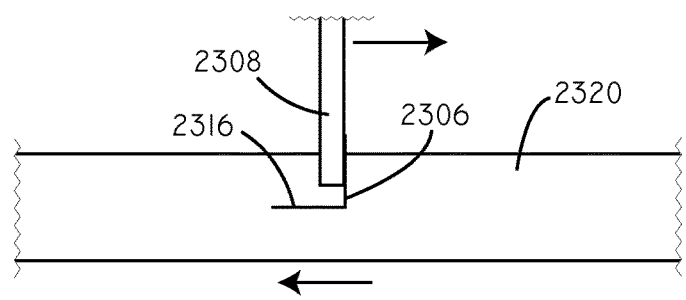
FIG. 25 is a schematic top view of a fluid applicator interfacing with a balloon catheter in accordance with various embodiments.
Figure 26:
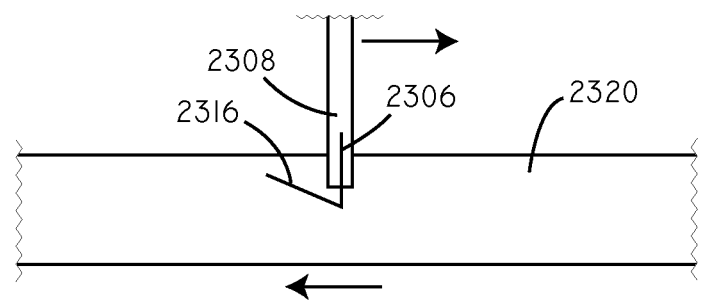
FIG. 26 is a schematic top view of a fluid applicator interfacing with a balloon catheter in accordance with various embodiments.

In this view, the fluid distribution bar 2306 is shown connected to the top side of the fluid applicator 2308. However, it will be appreciated that the fluid distribution bar 2306 can also be connected to the sides, bottom, or any other portion of the fluid applicator in other embodiments. In still other embodiments, the fluid distribution bar is not connected to the fluid applicator at all. FIG. 24 is a schematic top view of the fluid applicator 2308 and fluid distribution bar 2306 interfacing with the surface 2320 balloon catheter.

While the embodiment shown in 24 illustrates an embodiment of a fluid distribution bar 2306 that is substantially straight, it will be appreciated that in other embodiments the fluid distribution bar can be curved and/or have bent portions. 25 a schematic top view of a fluid applicator interfacing with a balloon catheter is shown in accordance with another embodiment. The coating apparatus includes a fluid distribution bar 2306 that is connected to the fluid applicator 2308 and is arranged to contact the surface 2320 of the balloon catheter. The fluid distribution bar 2306 also includes a portion 2316 (or tail) that is angled with respect to the major axis of the fluid applicator. The portion 2316 extends in a direction that is downstream of the fluid applicator (e.g. on the side of the fluid applicator where coating material has already been deposited based on how the fluid applicator and/or the device to be coated move with respect to one another). However, in other embodiments, the portion 2316 could extend upstream of the fluid applicator.

Figure 27:
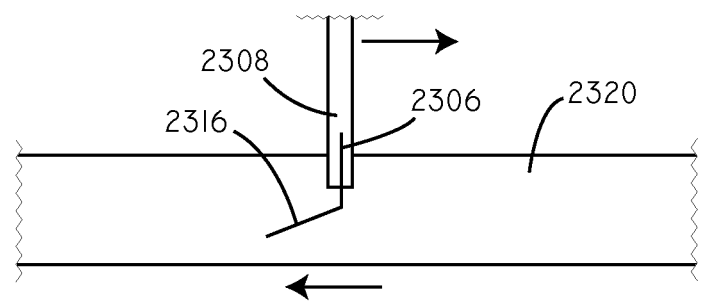
FIG. 27 is a schematic top view of a fluid applicator interfacing with a balloon catheter in accordance with various embodiments.

In some embodiments the portion 2316 can be substantially parallel with the lengthwise axis of the device to be coated, such as the balloon catheter. In other embodiments, the portion 2316 can be angled with respect to the lengthwise axis of the device to be coated. 26, a schematic top view is shown of a fluid applicator interfacing with a balloon catheter in accordance with various embodiments. The coating apparatus includes a fluid distribution bar 2306 that is connected to the fluid applicator 2308 and is arranged to contact the surface 2320 of the balloon catheter. The fluid distribution bar 2306 includes a portion 2316 that is angled back toward the fluid applicator 2308. FIG. 27 shows another embodiment of the coating apparatus. In this view, the fluid distribution bar 2306 includes a portion 2316 that is angled away from the fluid applicator 2308.

Figure 28:
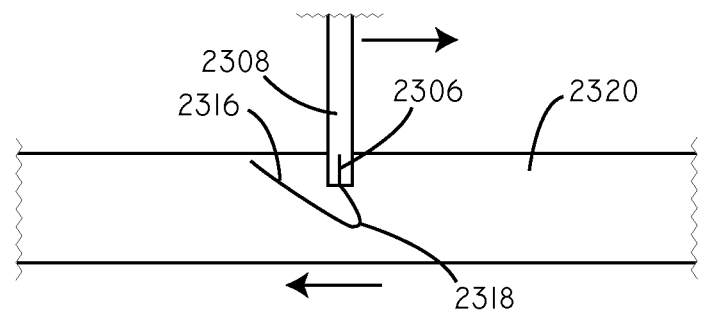
FIG. 28 is a schematic top view of a fluid applicator interfacing with a balloon catheter in accordance with various embodiments.
Figure 29:
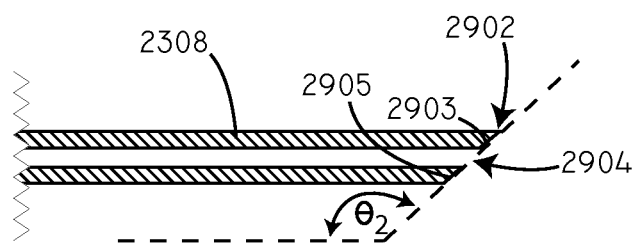
FIG. 29 is a schematic cross-sectional view of a fluid applicator.

FIG. 28 is a schematic top view of a fluid applicator interfacing with a balloon catheter in accordance with another embodiment. The coating apparatus includes a fluid distribution bar 2306 that is connected to the fluid applicator 2308 and is arranged to contact the surface 2320 of the balloon catheter. The fluid distribution bar 2306 includes a portion 2318 that is disposed upstream of the fluid applicator and a portion 2316 that is disposed downstream of the fluid applicator.

It will be appreciated that the fluid distribution bar can be made of various materials. In some embodiments it can be formed of polymers, metals, composites, ceramics and the like. In some embodiments it is flexible. In other embodiments it is substantially rigid. In some embodiments it can have a diameter that is less than the diameter of the fluid applicator. In some embodiments it is circular in cross sectional. In other embodiments it can be polygonal, ovoid, or irregular in cross-section. In some embodiments it can have a flattened surface where it contacts the device to be coated.

It will be appreciated that coating solutions applied onto balloons can include various components including, but not limited to, one or more active agents, carrier agents and/or solvents, polymers (including degradable or non-degradable polymers), excipients, and the like. The relative amounts of the components of the coating solution will depend on various factors including the desired amount of active agent to be applied to the balloon and the desired release rate of the active agent.

Embodiments herein include methods of applying coatings onto balloon catheters. In an embodiment, the method can include rotating a balloon catheter with a rotation mechanism, the balloon catheter comprising a balloon, contacting the balloon with a movement restriction structure defining a channel, wherein the channel limits lateral movement of the balloon, applying a coating solution onto the surface of the balloon with a fluid applicator (such as through direct contact with a fluid applicator), contacting the surface of the balloon with a fluid distribution bar, and blowing a stream of a gas onto the surface of the balloon. In some embodiments, the balloon catheter can be rotated at a speed of between 100 and 400 rotations per minute.

In some embodiments, the method can include moving the fluid applicator relative to the lengthwise axis of the drug eluting balloon catheter. In some embodiments, the method can include moving the drug eluting balloon catheter along its lengthwise axis relative to the fluid applicator, fluid distribution bar, and movement restriction structure.

29, a schematic cross-sectional view is show of a fluid applicator 2308. The fluid applicator 2308 can include a tip 2902 having a face 2904 (or surface) that is angled with respect to the lengthwise axis of the fluid applicator 2308.

The face 2904 can extend all the way across the width of the tip 2902 in some embodiments. In some embodiments, a line that connects the top portion 2903 of the tip 2902 with the bottom portion 2905 of the tip 2902 (or the line is parallel to the face 2904 of the tip 2902) can have an angle $\theta_2$ with respect to a line parallel to the lengthwise axis of the fluid applicator 2308. In some embodiments, angle $\theta_2$ can be from about 95 to about 175 degrees. In some embodiments, Angle $\theta_2$ can be from about 105 to about 165 degrees. In some embodiments, Angle $\theta_2$ can be from about 115 to about 155 degrees. In some embodiments, Angle $\theta_2$ can be from about 125 to about 145 degrees. In some embodiments, Angle $\theta_2$ can be from about 130 to about 140 degrees.

Figure 30:
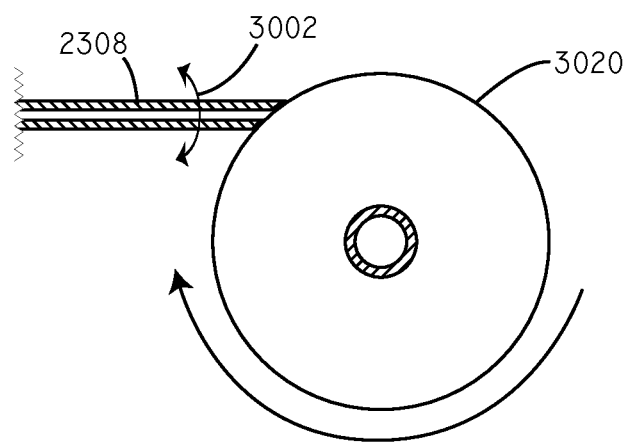
FIG. 30 is a schematic view of a fluid applicator interfacing with a surface of a device to be coated.

FIG. 30 shows a view of the fluid applicator 2308 interfacing with a surface 3020 of a device to be coated, such as a balloon catheter. The fluid applicator 2308 can be configured to rotate around its lengthwise axis as indicated by arrow 3002. In some embodiments, the fluid applicator 2308 can be connected to a rotation mechanism to cause it to rotate.

Figure 31:
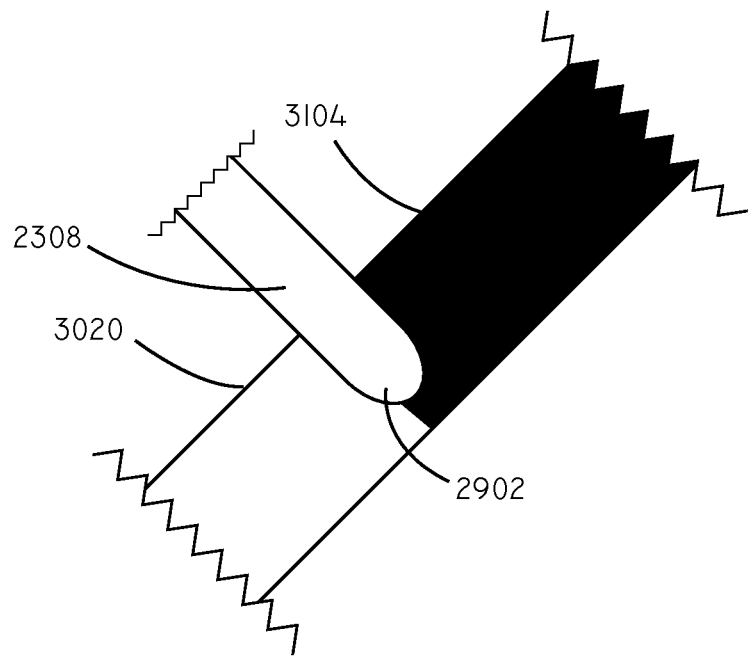
FIG. 31 is a schematic top view of a fluid applicator interfacing with a surface of a device to be coated.
Figure 32:
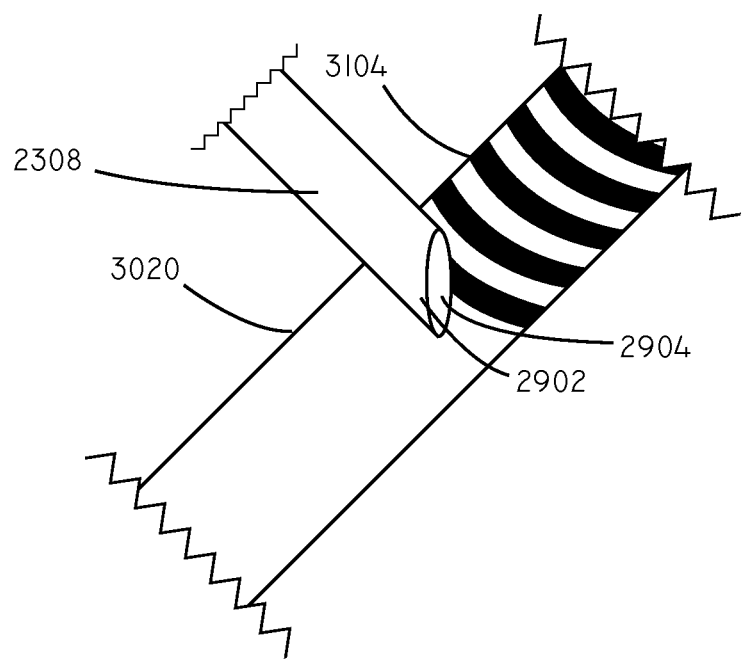
FIG. 32 is a schematic top view of a fluid applicator interfacing with a surface of a device to be coated.

Referring now to FIG. 31, a schematic top view is shown of a fluid applicator 2308 interfacing with a surface 3020 of a device to be coated. In this view, the face of the fluid applicator 2308 is oriented downward toward the surface 3020 consistent with the orientation shown in FIG. 30. It has been found that this orientation of the tip face 2904 results in a coating 3104 being applied that is substantially continuous in coverage. 32, a schematic top view is shown of a fluid applicator 2308 interfacing with a surface 3020 of a device to be coated wherein the face 2904 of the tip 2902 is oriented differently than as shown in FIG. 31. In this view, the fluid applicator 2308 has been rotated approximately 90 degrees such that the face 2904 of the tip 2902 is now facing approximately sideward with respect to the surface 3020. It has been found that this orientation of the tip face 2904 results in a coating 3104 being applied that is discontinuous in coverage and forms a spiral or helical shape.

The degree of rotation of the fluid applicator 2308 can vary. By way of example, in some embodiments, the fluid applicator 2308 can be rotated from about 10 degrees to about 350 degrees. In some embodiments, the fluid applicator 2308 can be rotated from about 10 degrees to about 170 degrees. In some embodiments, the fluid applicator 2308 can be rotated from about 45 degrees to about 135 degrees. In some embodiments, the fluid applicator 2308 can be rotated from about 60 degrees to about 120 degrees. In some embodiments, the fluid applicator 2308 can be rotated from about 75 degrees to about 105 degrees. In some embodiments, the fluid applicator 2308 can be rotated from about 85 degrees to about 95 degrees. In some embodiments, the fluid applicator 2308 can be rotated about 90 degrees.

In various embodiments, the fluid applicator 2308 can be rotated to a particular orientation in order to create either a continuous or discontinuous coating as desired. In some embodiments, the fluid applicator 2308 can be rotated during a coating application process allowing for the creation of medical devices having segments of continuous coating coverage and segments with discontinuous coating coverage.

Figure 33:
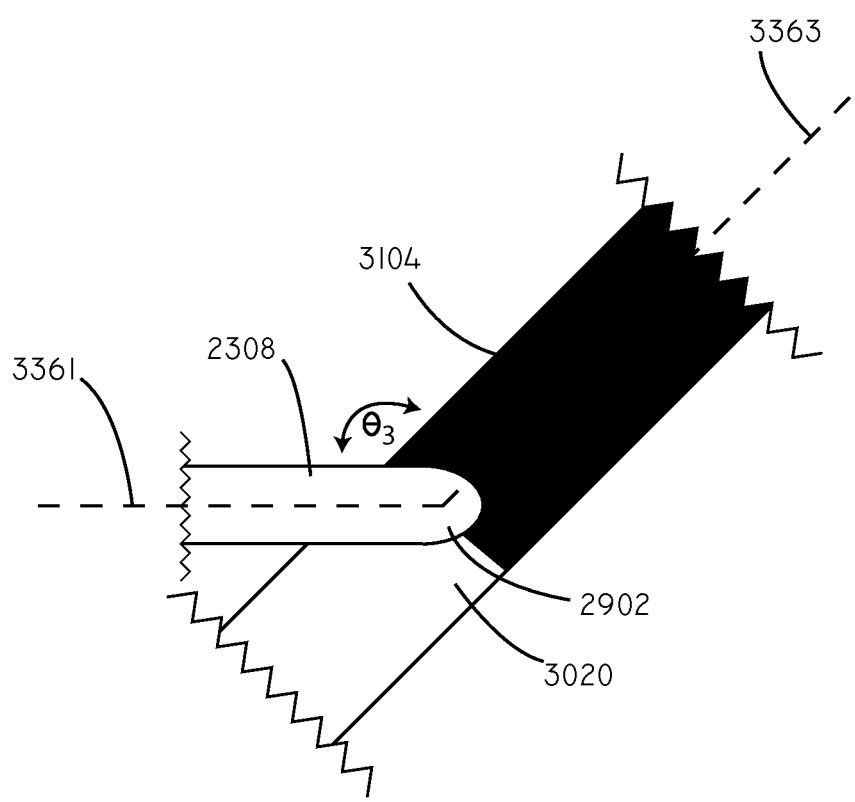
FIG. 33 is a schematic top view of a fluid applicator interfacing with a surface of a device to be coated.

Referring now to FIG. 33, a schematic top view is shown of a fluid applicator 2308 interfacing with a surface 3020 of a device to be coated. In this view, the lengthwise axis 3361 of the fluid applicator 2308 forms an angle $\theta_3$ with respect to the lengthwise axis 3363 of the device to be coated. In specific, angle $\theta_3$ can be from about 0 to about 180 degrees. In some embodiments, angle $\theta_3$ can be from about 20 to about 160 degrees. In some embodiments, angle $\theta_3$ can be from about 45 to about 135 degrees. In some embodiments, angle $\theta_3$ can be from about 70 to about 110 degrees. In some embodiments, angle $\theta_3$ can be from about 85 to about 95 degrees. In some embodiments, angle $\theta_3$ can be about 90 degrees. In some embodiments, angle $\theta_3$ can be from about 115 degrees to about 155 degrees. In some embodiments, angle $\theta_3$ can be from about 125 degrees to about 145 degrees.

Figure 34:
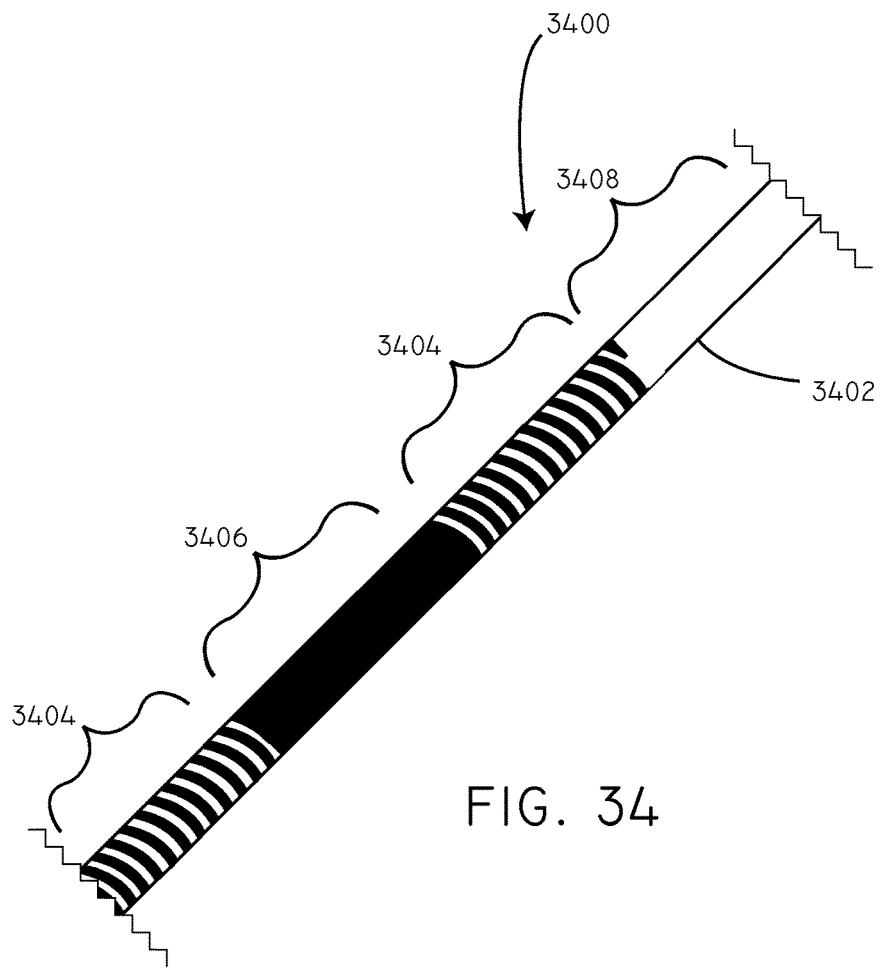
FIG. 34 is a schematic view of a portion of a medical device in accordance with various embodiments herein.

Referring now to FIG. 34, a schematic view is show of a portion of a medical device 3400 having a surface 3402. The surface 3402 includes a segment 3406 with continuous coating coverage and segments 3404 with discontinuous coating coverage. The segment with discontinuous coating coverage can have various shaped coating configurations such as spiral, helical, ring, and the like. In some embodiments, the surface 3402 can also include a segment 3408 with no coating coverage.

It will be appreciated that the segments can be aligned with various features of the device to be coated. By way of example, to decrease the amount of coating material in an area near the ends of a balloon on a balloon catheter, the fluid applicator can be rotated during the coating process to produce a discontinuous coating segment when approaching the ends of the balloon.

Figure 35:
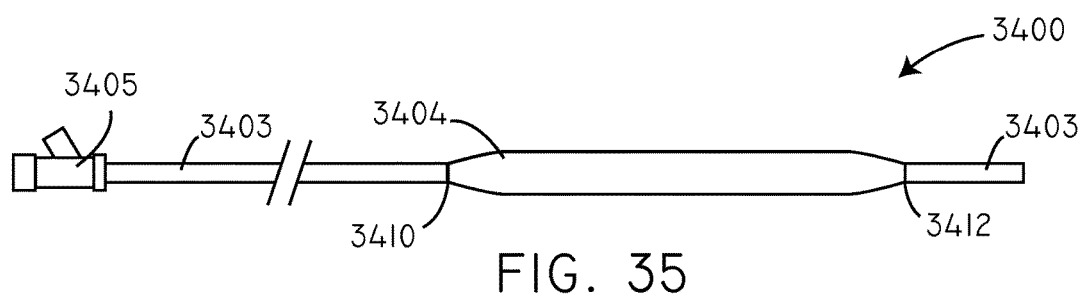
FIG. 35 is a schematic view of a medical device in accordance with various embodiments herein.

Referring now to FIG. 35, a schematic view of a medical device 3400 is shown. The medical device 3400 can optionally include a connection manifold 3405, a shaft 3403 having a surface, and an expandable portion 3404 (such as a balloon) having a surface. The expandable portion 3404 can include a proximal end 3410 and a distal end 3412. Coating segments, such as those shown in FIG. 34, can be disposed onto one or more of the shaft 3403 and the expandable portion 3404. In some embodiments, the expandable portion 3404 can include multiple coating segments thereon disposed adjacently to one another. By way of example, the expandable portion 3404 can include both continuous coating coverage segments and discontinuous coating coverage segments.

In some embodiments, the medical device 3400 can include at least one continuous coverage segment and at least two discontinuous coverage segments in some embodiments. In some embodiments, the discontinuous coverage segment can be disposed over at least one of the distal end and the proximal end. In some embodiments, a first discontinuous coverage segment can be disposed over the proximal end and a second discontinuous coverage segment can be disposed over the distal end. In some embodiments, the continuous coverage segment can be disposed over the expandable portion between the distal end and the proximal end.

In various embodiments, a method of coating a medical device is included. The method can include rotating a medical device to be coated with a rotation mechanism. In some embodiments, the medical device can be a balloon catheter comprising a balloon. The method can further include contacting the surface of the medical device with a fluid applicator, applying a coating solution onto the surface of the balloon with the fluid applicator, and rotating the fluid applicator axially about its lengthwise major axis.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A coating apparatus comprising:
a coating application unit comprising
a fluid applicator having a lengthwise axis and a width, the fluid applicator comprising a tip, the tip comprising a face across the width of the fluid applicator, the face oriented at an angle of from about 15 to about 75 degrees with respect to the lengthwise axis of the fluid applicator, the fluid applicator configured to rotate around its lengthwise axis;
a rotation mechanism; and
an axial motion mechanism, the axial motion mechanism configured to cause movement of at least one of the coating application unit and the rotation mechanism with respect to one another.

2. The coating apparatus of claim 1, wherein the coating application unit is configured to remain stationary and the rotation mechanism is configured to move.

3. The coating apparatus of claim 1, wherein the rotation mechanism is configured to remain stationary and the coating application unit is configured to move.

4. The coating apparatus of claim 1, wherein the rotation mechanism comprises an electric motor.

5. The coating apparatus of claim 1, further comprising a fluid reservoir in fluid communication with the fluid applicator.

6. The coating apparatus of claim 5, further comprising a fluid pump in fluid communication with the fluid reservoir and the fluid applicator.

7. The coating apparatus of claim 6, further comprising a controller configured to control the fluid pump and the rotation mechanism.

8. The coating apparatus of claim 1, the fluid applicator comprising a polymeric tube.

9. The coating apparatus of claim 1, wherein the rotation mechanism is configured to rotate a drug eluting balloon catheter.

10. The coating apparatus of claim 1, the coating application unit further comprising a fluid distribution bar.

11. The coating apparatus of claim 1, the coating application unit further comprising a movement restriction structure.

12. The coating apparatus of claim 11, wherein the movement restriction structure is configured to prevent lateral movement of the drug eluting balloon catheter as it is being rotated by the rotation mechanism.

13. The coating apparatus of claim 12, the movement restriction structure defining a channel surrounding the drug eluting balloon catheter.

14. The coating apparatus of claim 12, the movement restriction structure defining a channel having a size sufficient to surround the balloon of the drug eluting balloon catheter when the balloon is in an expanded state.

15. The coating apparatus of claim 12, the movement restriction structure defining a channel surrounded by the movement restriction structure in a radially continuous manner.

16. The coating apparatus of claim 12, the movement restriction structure defining a channel surrounded by the movement restriction structure in a radially non-continuous manner.

17. The coating apparatus of claim 12, the movement restriction structure comprising a first body member and a second body member, the first body member defining a first portion of a channel and the second body member defining a second portion of a channel, the first body member and second body member separated from one another by a distance of at least 3 millimeters.

18. The coating apparatus of claim 12, the movement restriction structure comprising a first body member and a second body member, the first body member defining a first portion of a channel and the second body member defining a second portion of a channel, the first body member and second body member configured to rotate between a closed position where a balloon is locked in place in the channel and an open position where the balloon is released.

19. The coating apparatus of claim 18, wherein the first body member and second body member are configured to rotate together around a single axis.

20. The coating apparatus of claim 18, wherein the first body member and second body member are configured to rotate independently from one another.

21. The coating apparatus of claim 1, wherein the axial motion mechanism is configured to create horizontal motion.

22. The coating apparatus of claim 1, wherein the axial motion mechanism is configured to create vertical motion.

* * * * *